US008945857B2

(12) United States Patent
Schrader

(10) Patent No.: US 8,945,857 B2
(45) Date of Patent: Feb. 3, 2015

(54) METHODS OF ISOLATING CELLS AND GENERATING MONOCLONAL ANTIBODIES

(76) Inventor: John Schrader, West Vancouver (CA)

( * ) Notice: Subject to any disclaimer, the term of this patent is extended or adjusted under 35 U.S.C. 154(b) by 1904 days.

(21) Appl. No.: 11/993,656

(22) PCT Filed: Jun. 30, 2006

(86) PCT No.: PCT/CA2006/001074
§ 371 (c)(1),
(2), (4) Date: May 5, 2010

(87) PCT Pub. No.: WO2007/003041
PCT Pub. Date: Jan. 11, 2007

(65) Prior Publication Data
US 2010/0255496 A1 Oct. 7, 2010

Related U.S. Application Data

(60) Provisional application No. 60/695,547, filed on Jul. 1, 2005.

(51) Int. Cl.
*G01N 33/53* (2006.01)
*G01N 31/00* (2006.01)
*C07K 16/00* (2006.01)
*C07K 16/10* (2006.01)

(52) U.S. Cl.
CPC ............ *C07K 16/00* (2013.01); *C07K 16/1018* (2013.01); *C07K 2317/21* (2013.01); *Y10S 530/808* (2013.01)
USPC ................ 435/7.21; 435/2; 435/6.1; 435/7.1; 435/7.24; 435/7.25; 435/7.5; 435/7.8; 435/69.6; 435/70.1; 435/70.21; 435/70.4; 435/326; 435/328; 436/63; 436/172; 436/503; 436/518; 436/519; 436/520; 436/522; 436/526; 436/528; 436/546; 436/547; 530/387.3; 530/388.1; 530/808; 424/130.1

(58) Field of Classification Search
CPC ........... C07K 2317/24; C07K 2317/92; A61K 39/3955; A61K 45/06; A61K 2039/505
USPC .............. 435/2, 6.1, 7.1, 7.24, 7.25, 7.5, 7.8, 435/69.6, 70.1, 70.21, 70.4, 326, 328; 436/503, 518, 519, 520, 522, 526, 528, 436/546, 547, 63, 172; 530/387.3, 388.1, 530/808
See application file for complete search history.

(56) References Cited

U.S. PATENT DOCUMENTS

| | | | | |
|---|---|---|---|---|
| 4,689,299 A * | 8/1987 | Insel et al. | | 435/340 |
| 5,213,960 A * | 5/1993 | Chang | | 435/2 |
| 5,326,696 A * | 7/1994 | Chang | | 435/7.24 |
| 5,627,052 A * | 5/1997 | Schrader | | 435/69.6 |
| 6,541,225 B1 * | 4/2003 | Li | | 435/69.6 |
| 2004/0198960 A1 * | 10/2004 | Janoff et al. | | 530/388.4 |
| 2004/0219611 A1 * | 11/2004 | Racher | | 435/7.5 |
| 2006/0148012 A1 * | 7/2006 | Brown et al. | | 435/7.23 |
| 2007/0037220 A1 * | 2/2007 | Burke et al. | | 435/7.2 |

FOREIGN PATENT DOCUMENTS

| | | |
|---|---|---|
| CA | 2090126 | 3/1992 |
| WO | WO 2004/051268 | 6/2004 |
| WO | 2005/042774 | 5/2005 |
| WO | 2005078450 | 8/2005 |

OTHER PUBLICATIONS

Hellström et al., 1985. In Monoclonal Antibodies for Cancer Detection and Therapy (Baldwin et al, eds.), Academic Press, London. p. 20.*
Medina, F., et al., "The heterogeneity shown by human plasma cells from tonsil, blood, and bone marrow reveals graded stages of increasing maturity, but local profiles of adhesion molecule expression", BLOOD, Mar. 15, 2002—vol. 99, No. 6, pp. 2154-2161.
Lakew, M., et al., "Combined immunomagnetic cell sorting and ELISPOT assay for the phenotypic characterization of specific antibody-forming cells", Journal of Immunological Methods, Elsevier Science Publishers B.V., Amsterdam, NL, vol. 203, No. 2, Apr. 25, 1997, pp. 193-198.
Harris, T.N., et al., "Electron microscopic observations on antibody-producing lymph node cells", The Journal of Experimental Medicine, Jan. 1, 1966, vol. 123, No. 1, pp. 161-172, plates 27-32.
Arce, S. et al., "CD38 low IgG-secreting cells are precursors of various CD38 high-expressing plasma cell populations", Journal of Leukocyte Biology, vol. 75, No. 6, Jun. 2004, pp. 1022-1028.
Wood-BL et al., "Handbook of Diagnostic Hematopathology Tests", Feb. 2001, Department of Laboratory Medicine, University of Washington, retrieved from the internet: URL: http://depts.washington.edu/labweb/PatientCare/Clinical/Guides/hemato.pdf.
Scibelli, A. et al., "Fast track selection of immunogens for novel vaccines through visualisation of the early onset of the B-cell response", Vaccine, Butterworth Scientific. Guildford, GB, vol. 23, No. 16, Mar. 14, 2005, pp. 1900-1909.
Heilmann, C., et al. "Quantitation of Blood Lymphocytes Secreting Antibodies to Pneumococcal Polysaccharides after in Vivo Antigenic Stimulation", Scand. J. Immunol., 1986, vol. 23, pp. 189-194.
Babcook, J.S., et al., "A Novel Strategy for Generating Monoclonal Antibodies from Single, Isolated Lymphocytes Producing Antibodies of Defined Specificities", Proc. Natl. Acad. Sci. USA., 1996, vol. 93, pp. 7843-7848.
Odendahl, M. et al., "Generation of Migratory Antigen-Specific Plasma Blasts and Mobilization of Resident Plasma Cells in a Secondary Immune Response", Blood, 2005, vol. 105, No. 4, pp. 1614-1621.
Townsend, S.E. et al., "Single Epitope Multiple Staining to Detect Ultraflow Frequency B Cells", J. Immunol. Methods, 2001, vol. 249, No. 1-2, pp. 137-146.

(Continued)

*Primary Examiner* — Lisa Cook
(74) *Attorney, Agent, or Firm* — Bereskin & Parr LLP; Melanie Szweras

(57) ABSTRACT

The invention provides methods for isolating cells, particularly antibody-secreting cells that have a high likelihood of secreting antibodies specific for a desired antigen for the purpose of making monoclonal antibodies.

16 Claims, 3 Drawing Sheets

(56) References Cited

OTHER PUBLICATIONS

Wrammert, J., et al., "Broadly cross-reactive antibodies dominate the human B cell response against 2009 pandemic H1N1 influenza virus infection", J. Exp. Med. Jan. 2011, vol. 208, No. 1, pp. 181-193.

Newman J et al: "Identification of an antigen-specific B cell population", Journal of Immunological Methods, Elsevier Science Publishers B.V., Amsterdam, NL, vol. 272, No. 1-2, Jan. 2003, pp. 177-187.

Baumgarth Nicole: "B-cell immunophenotyping", Methods in Cell Biology, 2004, vol. 75, pp. 643-662.

Wood Brent: "Multicolor immunophenotyping: human immune system hematopoiesis.", Methods in Cell Biology, vol. 75, 2004, pp. 559-576.

Baumgarth Nicole et al: "Optimization of emission optics for multicolor flow cytometry", Methods in Cell Biology, vol. 75, 2004, pp. 3-22.

Doucett Virginia P et al: "Enumeration and characterization of virus-specific B cells by multicolor flow cytometry", Journal of Immunological Methods, vol. 303, No. 1-2, Aug. 2005, pp. 40-52.

Masahiro Tomita et al., Selective Production of Hybridoma Cells: Antigenic-Based Pre-Selection of B Lymphocytes for Electrofusion with Myeloma Cells. Biochimica et Biophysica Acta, 1055 (1990) 199-206 Elsevier.

Christopher C. Goodnow, Multistep Pathogenesis of Autoimmune Disease, Cell 130:25-35, Jul. 13, 2007.

Jens Wrammert et al., Rapid Cloning of High-Affinity Human Monoclonal Antibodies Against Influenza Virus, Nature, vol. 453, 667-671 (May 29, 2008).

J.A. Coronella et al., Amplification of IgG VH and VL (Fab) from Single Human Plasma Cells and B Cells, Nucleic Acids Research, vol. 28, No. 20 e85:1-7, 2000.

\* cited by examiner

FIGURE 2

Sequences of variable regions of genes encoding the variable regions of the heavy and light chains of two rabbit antibodies, D10 and E5, binding to a Fab fragment of human immunoglobulin MJ5

D10
>D10 Kappa (SEQ ID NO:13)
```
atggacacgagggcccccactcagctgctggggctcctgctgctctggctcccaggtgccagatgtgccgt
cgtgatgacccagactgcatccccgtgtctgcagctgtgggaggcacagtcaccatcaattgccaggcca
gtgagaccatttataatagtttagcctggtatcagcagaagccagggcagcctcccaagctcctgatctac
agggcatccactctggcatctggggtcccatcgcggttcagcggcagtggatctgggacagagtacactct
caccatcagcgacctggagtgcgacgatgctgccacttactactgtcaatgtacttattatggttgtggag
ttgctttcggcggagggaccgaggtggtggtcaaaactgcggccgca
```

>D10 Heavy (SEQ ID NO:14)
```
atggagactgggctgcgctggcttctcctggtcgctgtgctcaaaggtgtccagtgtcagtcagtgaagga
gtccgagggaggtctctttaagccaacggataccctgacactcacctgcacagtctctggattctccctca
gtagtcatgcaataagctgggtccgccaggctcccgggaacgggctggaatggatcggaatcattgatgat
catgataacacgtactacgcgacctgggcgacaagccggtccaccatcaccagaaacaccaacgagaacac
ggtgactctgaaaatgaccagtctgacagccgcggacacggccacctatttctgtgcgacagagggttata
attttccttatctctttaacatctggggcccgggcaccctcgtcaccgtctcttcagcaagcttt
```

E5
>E5 Kappa (SEQ ID NO:15)
```
atggacacgagggcccccactcagctgctggggctcctgctgctctggctcccaggtgtcacatttgctca
agtgctgacccagactccatccctgtgtctgcagctgtgggaggcacagtcaccatcaattgccaggcca
gtcagagtgttgttaataagaactacttagcctggtatcagcagaaaccagggcagcctcccaagctcctg
atctatggtgcatccactctggcatctggggtcgcatcgcggttcagcggcagtggatctgggacacagtt
cactctcaccatcagcggcgtgcagtgtgacgatgctgccacttactactgtcaaggcacttatcggagtg
atgtttggtactttggtttcggcggagggaccgaggtggtggtcaaaactgcggccgcacca
```

>E5 Heavy (SEQ ID NO:16)
```
atggagactgggctgcgctggcttctcctggtcgctgtgctcaaaggtgtccagtgccagtcggtggagga
gtccggggggtcgcctggtcacgcctgggacacccctgacactcacctgcacagtctctggattctccctca
gcatctacgacatgtgctgggtccgccaggctccagggaaggggctggagtggatcggatacattagttat
ggtggtagcgcatactacgcgagctgggcgaaaggccgattcaccatctccaaaacctcgaccacggtgga
tctgaagatcgccagtccgacaaccgaggacacggccacctatttctgtgccaggggatatactggatata
gtgtttttgatggttttgatccctggggcccaggcaccctggtcaccgtctcctcagcaagcttc
```

ELISA assay of binding to human Fab of supernatants of 293 cells transfected with paired H - and L-chains incorporating V region genes from clones of rabbit ASC

SEQUENCE LISTING

<160> NUMBER OF SEQ ID NOS: 16

<210> SEQ ID NO 1
<211> LENGTH: 38
<212> TYPE: DNA
<213> ORGANISM: Artificial Sequence
<220> FEATURE:
<223> OTHER INFORMATION: primer

<400> SEQUENCE: 1
gcagctagcc accatggaca cgagggcccc cactcagc                38

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
tggtgggaag atgaggacag tagg                24

<210> SEQ ID NO 3
<211> LENGTH: 36
<212> TYPE: DNA
<213> ORGANISM: Artificial Sequence
<220> FEATURE:
<223> OTHER INFORMATION: primer

<400> SEQUENCE: 3
atagcggccg cagttttgat ttctaccttg gtgcca                36

<210> SEQ ID NO 4
<211> LENGTH: 35
<212> TYPE: DNA
<213> ORGANISM: Artificial Sequence
<220> FEATURE:
<223> OTHER INFORMATION: primer

<400> SEQUENCE: 4
atagcggccg cagttttgac caccacctcg gtccc                35

<210> SEQ ID NO 5
<211> LENGTH: 35
<212> TYPE: DNA
<213> ORGANISM: Artificial Sequence
<220> FEATURE:
<223> OTHER INFORMATION: primer

<400> SEQUENCE: 5
atagcggccg cagttttgat ttccagtttg gtccc                35

<210> SEQ ID NO 6
<211> LENGTH: 35
<212> TYPE: DNA
<213> ORGANISM: Artificial Sequence
<220> FEATURE:
<223> OTHER INFORMATION: primer

<400> SEQUENCE: 6
atagcggccg cagttttgat ctccaccatg gtccc                35

<210> SEQ ID NO 7
<211> LENGTH: 35

-continued

```
<212> TYPE: DNA
<213> ORGANISM: Artificial Sequence
<220> FEATURE:
<223> OTHER INFORMATION: primer

<400> SEQUENCE: 7
atagcggccg cagttttgat ctccagcttg gtctc                                  35

<210> SEQ ID NO 8
<211> LENGTH: 37
<212> TYPE: DNA
<213> ORGANISM: Artificial Sequence
<220> FEATURE:
<223> OTHER INFORMATION: primer

<400> SEQUENCE: 8
tcggctagcc accatggaga ctgggctgcg ctggctt                                37

<210> SEQ ID NO 9
<211> LENGTH: 28
<212> TYPE: DNA
<213> ORGANISM: Artificial Sequence
<220> FEATURE:
<223> OTHER INFORMATION: primer

<400> SEQUENCE: 9
ggccagtggg aagactgacg gagcctta                                          28

<210> SEQ ID NO 10
<211> LENGTH: 32
<212> TYPE: DNA
<213> ORGANISM: Artificial Sequence
<220> FEATURE:
<223> OTHER INFORMATION: primer

<400> SEQUENCE: 10
ataaagcttg ctgaagagat ggtgaccagg gt                                     32

<210> SEQ ID NO 11
<211> LENGTH: 32
<212> TYPE: DNA
<213> ORGANISM: Artificial Sequence
<220> FEATURE:
<223> OTHER INFORMATION: primer

<400> SEQUENCE: 11
ataaagcttg ctgaggagac ggtgaccagg gt                                     32

<210> SEQ ID NO 12
<211> LENGTH: 32
<212> TYPE: DNA
<213> ORGANISM: Artificial Sequence
<220> FEATURE:
<223> OTHER INFORMATION: primer

<400> SEQUENCE: 12
ataaagcttg ctgaagagac ggtgacgagg gt                                     32

<210> SEQ ID NO 13
<211> LENGTH: 402
<212> TYPE: DNA
<213> ORGANISM: Oryctolagus cuniculus

<400> SEQUENCE: 13
atggacacga gggcccccac tcagctgctg gggctcctgc tgctctggct cccaggtgcc      60
```

| | |
|---|---|
| agatgtgccg tcgtgatgac ccagactgca tcccccgtgt ctgcagctgt gggaggcaca | 120 |
| gtcaccatca attgccaggc cagtgagacc atttataata gtttagcctg gtatcagcag | 180 |
| aagccagggc agcctcccaa gctcctgatc tacagggcat ccactctggc atctggggtc | 240 |
| ccatcgcggt tcagcggcag tggatctggg acagagtaca ctctcaccat cagcgacctg | 300 |
| gagtgcgacg atgctgccac ttactactgt caatgtactt attatggttg tggagttgct | 360 |
| ttcggcggag ggaccgaggt ggtggtcaaa actgcggccg ca | 402 |

<210> SEQ ID NO 14
<211> LENGTH: 420
<212> TYPE: DNA
<213> ORGANISM: Oryctolagus cuniculus

<400> SEQUENCE: 14

| | |
|---|---|
| atggagactg ggctgcgctg gcttctcctg gtcgctgtgc tcaaaggtgt ccagtgtcag | 60 |
| tcagtgaagg agtccgaggg aggtctcttt aagccaacgg ataccctgac actcacctgc | 120 |
| acagtctctg gattctcccct cagtagtcat gcaataagct gggtccgcca ggctcccggg | 180 |
| aacgggctgg aatggatcgg aatcattgat gatcatgata acacgtacta cgcgacctgg | 240 |
| gcgacaagcc gtccaccat caccagaaac accaacgaga cacggtgac tctgaaaatg | 300 |
| accagtctga cagccgcgga cacggccacc tatttctgtg cgacagaggg ttataatttt | 360 |
| ccttatctct ttaacatctg gggcccgggc accctcgtca ccgtctcttc agcaagcttt | 420 |

<210> SEQ ID NO 15
<211> LENGTH: 417
<212> TYPE: DNA
<213> ORGANISM: Oryctolagus cuniculus

<400> SEQUENCE: 15

| | |
|---|---|
| atggacacga gggcccccac tcagctgctg gggctcctgc tgctctggct cccaggtgtc | 60 |
| acatttgctc aagtgctgac ccagactcca tccctgtgt ctgcagctgt gggaggcaca | 120 |
| gtcaccatca attgccaggc cagtcagagt gttgttaata gaaactactt agcctggtat | 180 |
| cagcagaaac cagggcagcc tcccaagctc ctgatctatg gtgcatccac tctggcatct | 240 |
| ggggtcgcat cgcggttcag cggcagtgga tctgggacac agttcactct caccatcagc | 300 |
| ggcgtgcagt gtgacgatgc tgccacttac tactgtcaag gcacttatcg gagtgatgtt | 360 |
| tggtactttg gttcggcgg agggaccgag gtggtggtca aaactgcggc cgcacca | 417 |

<210> SEQ ID NO 16
<211> LENGTH: 420
<212> TYPE: DNA
<213> ORGANISM: Oryctolagus cuniculus

<400> SEQUENCE: 16

| | |
|---|---|
| atggagactg ggctgcgctg gcttctcctg gtcgctgtgc tcaaaggtgt ccagtgccag | 60 |
| tcggtggagg agtccggggg tcgcctggtc acgcctggga caccctgac actcacctgc | 120 |
| acagtctctg gattctcccct cagcatctac gacatgtgct gggtccgcca ggctccaggg | 180 |
| aaggggctgg agtggatcgg atacattagt tatggtggta cgcatacta cgcgagctgg | 240 |
| gcgaaaggcc gattcaccat ctccaaaacc tcgaccacgg tggatctgaa gatcgccagt | 300 |
| ccgacaaccg aggacacggc cacctatttc tgtgccaggg gatatactgg atatagtgtt | 360 |
| tttgatggtt ttgatccctg gggcccaggc accctggtca ccgtctcctc agcaagcttc | 420 |

METHODS OF ISOLATING CELLS AND GENERATING MONOCLONAL ANTIBODIES

FIELD OF THE INVENTION

The invention relates to methods of isolating cells, particularly antibody-secreting and antibody-forming cells, and methods of using these cells to make monoclonal antibodies.

BACKGROUND OF THE INVENTION

There are known methods for generating monoclonal antibodies that are based on the isolation of B lymphocytes that produce antibodies targeting a particular antigen. These methods depend on the use of purified antigen or a mixture of antigens to identify and isolate B lymphocytes that bind that antigen (or antigens). Methods that depend on the use of antigen or mixtures of antigens to select antibody-forming cells (AFC) or B lymphocytes that express surface-receptors specific for an antigen, include using antigen-coated magnetic beads (Lagerkvist et al., 1995) or fluorochrome-labelled antigens and fluorescence activated cell-sorting (FACS) (Weitkamp et al., 2003) to isolate cells which have then been commonly expanded into clones. Monoclonal antibodies are then generated from these clones, for example by fusion to generate hybridomas (Steenbakkers et al., 1993) or by cloning of the genes encoding the antibody variable regions (e.g. using RT-PCR) (Lagerkvist et al., 1995; Wang & Stollar, 2000; Weitkamp et al., 2003). Alternatively, methods have been described to identify individual cells that are secreting antibody specific for a particular antigen, including using a hemolytic plaque assay with antigen-coupled erythrocytes, after which techniques such as RT-PCR can be used to clone the genes encoding the antibody variable regions (Babcook et al., 1996; U.S. Pat. No. 5,627,052 (1997) Schrader, J. W.). However, these strategies of identifying cells synthesizing antibodies specific for an antigen are not suitable for the generation of monoclonal antibodies against many desired target antigens, such as growth factor-receptors or other structures on the plasma membrane of cells that are not easy or possible to prepare in sufficient quantities in a pure or in a native state (e.g. native conformation may depend on appropriate post-translational modifications such as glycosylation). The state of the antigen is an important consideration because, for many applications, it is important to generate monoclonal antibodies that recognize the protein in its native configuration, for example if it is desired to generate an antibody that will neutralize a virus or toxin or bind some other biologically active substance. Moreover, methods that depend on isolating AFC using binding to specific antigen are not readily applied to the generation of libraries of monoclonal antibodies specific for the various unknown components of complex mixtures of substances such as those that occur on the surface of cells or viruses, or which are contained in a mixture of unknown compositions. Moreover, as described and currently practiced, methods based on the isolation of AFC using binding to antigen are confounded by failure to exclude cells that have bound antigen non-specifically, and from failure to exclude inadvertent co-isolation of the desired AFC together with a cell making a different antibody.

SUMMARY OF THE INVENTION

The present invention provides methods of isolating antibody-secreting cells (ASC) that have a high likelihood of secreting antibodies specific for a desired antigen and of generating ASC or clones of ASC from antibody-forming cells, and using these ASC that are secreting antibodies specific for a desired antigen, to generate monoclonal antibodies. The methods can be applied to the generation of monoclonal antibodies from any species that makes antibodies.

One key aspect of the invention is that the methods of the invention exploit the fact that at a certain interval during an immune response against an antigen or antigen-mixture the numbers of ASC in the blood (and certain other tissues) greatly increase and a relatively high percentage of these increased numbers of ASC are synthesizing and secreting antibodies specific for the antigens against which the animal is responding. Thus, to obtain cells that are making antibodies specific for antigens against which an animal's immune system has recently been exposed to or re-exposed to, it is only necessary to enrich cells with the general features characteristic of antibody-secreting cells (e.g. plasma blasts or plasma cells) because, with high frequency, these cells will be making antibodies with the desired specificity. Moreover, there are a number of well-known general characteristics of ASC discussed below, that distinguish them from other cells in the blood and these can be used with standard methods to purify and isolate single ASC. The enrichment of ASC making the antibodies specific for the desired antigens can thus be achieved without methods that depend on access to preparations of these antigens suitable for methods for isolating antigen-binding cells. The invention therefore can be used in cases where a preparation of the antigen(s) suitable for identification of antigen-binding cells is not available or where purification of the antigen(s) may damage or denature the natural configuration of the antigen(s), or where, as for example in the case of a disease of unknown cause, the antigens to which the immune system are responding is unknown. The isolation of monoclonal antibodies by this method thus may be a useful tool in characterizing the components of a mixture of antigens or the molecules present on the surface of a certain cell and in diagnosing and uncovering the nature of a disease. Moreover, ASC synthesize and secrete relatively large amounts of antibodies that can be collected in vitro and tested for their specificity for antigen.

Notwithstanding the above, there are situations where a suitable preparation of the antigen is available and where—with the new methods described—appropriately labeled antigen can be used to efficiently select cells that are secreting antibodies with the desired specificity, enabling recovery and copying of the genetic material that encoded the antigen-binding sites of the antibodies with the desired specificities. Therefore, another aspect of the invention involves the use of antigen to select ASC from recently immunized animals, as the recently generated ASC that enter the blood or other tissue usually exhibit samples of the antibody they make displayed as receptors for antigen on their surface (Odendahl et al., 2005). These cells contain relatively large amounts of mRNA encoding the specific antibody they make, facilitating the use of well-known techniques such as reverse transcription-polymerase chain reaction (RT-PCR) techniques to copy and clone the genetic material encoding the antigen-binding regions of the antibody. Alternatively, ASC may be fixed and permeabilized so that the capacity of the large amounts of intracellular antibodies to bind to the desired antigen can be detected by standard methods (e.g. flow cytometry) and used to select and isolate the cell for copying and cloning of the genetic material encoding the antigen-binding regions of the antibody. Moreover, the ASC that enter the blood during an active immune response still retain the capacity to multiply (Tangye et al., 2003) and thus can be expanded into clones thereby facilitating both the collection of the antibodies they are secreting for testing of their specificity for antigen, and the copying and cloning of the genetic information encoding the antigen-binding regions of the antibody. Finally, the invention includes methods that enable the hitherto problematic effective isolation of single antigen-binding memory B cells that occur at such low frequencies that they are hard to distinguish from the "background" of cells that non-specifically bind antigen, which makes their efficient isolation very difficult. The methods of the invention enable the isolation of these memory B cells, and use of these cells for the recovery of genetic information encoding the antigen-binding regions of the antibody they make either directly or following differentiation to ASC, with or without clonal expansion, enabling testing of the specificity of the antibody they make.

The methods of the invention exploit the fact that at certain times after exposure of an animal to antigen, samples of certain samples and tissues from recently immunized animals, in particular the blood, naturally contain enlarged populations of antibody-secreting cells in which a high proportion of the cells are secreting antibodies specific for the antigens involved in that ongoing immune response. Thus, it has been known that at certain times (e.g. between 4-10 days) after immunization, large numbers of cells enter the blood that are synthesizing and secreting antibodies specific for the antigens involved in that ongoing immune response (Barington et al., 1990a; Barington et al., 1990b; Heilmann et al., 1987; Heilmann & Pedersen, 1986; Bernasconi et al., 2002; Odendahl et al., 2005). At these times, newly generated ASC that are secreting antibodies specific for the immunizing antigen form a large proportion of the ASC present in the blood (Heilmann & Pedersen, 1986). Alternatively, a sample of a tissue (e.g. draining lymph-node or at a site of pathology where plasma cells accumulate in disease) from an animal undergoing an immune response to a mixture of antigens or an antigen is used as a source of cells forming antibodies against those antigens involved in the immune response. Finally, as described below, various well-known methods can be used to purify ASC (Odendahl et al., 2005; Horst et al., 2002). Moreover, these newly generated antibody-secreting cells that are making antibodies specific for antigens that provoked the ongoing immune response can be separated from other ASC that are secreting antibodies specific for other antigens that enter the blood during an immune response and have been displaced from niches in the bone marrow by the newly generated ASC (Odendahl et al., 2005). The invention also provides methods for selectively generating ASC that produce antibodies specific for a particular antigen.

The general characteristics of ASC that distinguish them from other cells in the same sample can be used to enrich them and isolate them. These characteristics include cell-surface markers, structural features and the ability to secrete antibodies, such as those specific for the immunizing antigen(s). Moreover, clones of antibody secreting cells that are secreting antibodies specific for the desired antigens can be generated by a method that enables purification of B lymphocytes that bind a particular antigen even though they are present in a population at only a very low frequency. The method of the invention does not necessarily depend on knowledge of the identity or chemical composition or nature of the antigens. These methods enable the generation of monoclonal antibodies specific for a desired antigen without the availability of a pure preparation of the desired antigen. Of particular value, the methods of the invention enable the generation of libraries of monoclonal antibodies against mixtures of substances including those on cells or membranes on the surface of cells. A person skilled in the art will appreciate that the methods of the invention are useful in greatly enhancing the efficiency and utility of strategies of generating monoclonal antibodies that utilize mixtures of antigens, which may be unknown, to enrich and isolate single antibody-secreting cells or clones thereof, or single antibody-forming cells which are used to generate clones of antibody-secreting cells.

The method of the invention ensures that only one single antibody-secreting cell or a clone of antibody-secreting cells making the same antibody is provided. This enables efficient cloning of genes encoding the antigen-binding sites of the antibody of the desired specificity.

One aspect of the invention is a method of isolating an antibody-secreting cell that has a high likelihood of secreting an antibody specific for a desired antigen, comprising the steps:
 a) providing a sample from an animal that was recently immunized with the desired antigen, wherein the sample comprises a population of antibody-secreting cells that are secreting antibodies specific for the desired antigen;
 b) increasing the concentration of antibody-secreting cells in the sample; and
 c) isolating an antibody-secreting cell.

Another aspect of the invention is a method of isolating an antibody-secreting cell that has a high likelihood of secreting an antibody specific for a desired antigen, comprising the steps:
 a) providing a sample from an animal that was recently immunized with the desired antigen, wherein the sample comprises a population of antibody-secreting cells that are secreting antibodies specific for the desired antigen;
 b) allowing cells in the sample to adhere to particles that are coated with an agent that captures antibodies secreted by the individual cells, such as Protein A or Protein G, or antibodies that bind to antibodies from the species of animal from which the sample was obtained; and
 c) identifying and isolating an antibody-secreting cell by detection of the captured antibodies using detectable reagents.

If a suitable preparation of antigen or a mixture of antigens is available, then these antigens can be used as the agent that captures secreted antibodies, instead of Protein A or Protein G, or antibodies that bind to antibodies from the species of animal from which the sample was obtained, or in a directly or indirectly labeled form, as an agent to identify cells that are associated with captured antibodies of the desired specificity.

Because they are highly specialized for the secretion of antibodies, ASC exhibit a variety of well-known characteristics that distinguish them from other cells in the blood and that can be used to enrich them and separate them from other cell-types in the sample. Without limitation these include a relative enlargement of the structures involved in antibody secretion, namely the endoplasmic reticulum and Golgi apparatus. Both structures will contain immunoglobulins. Moreover there are commercially available fluorescent dyes that stain the endoplasmic reticulum or Golgi apparatus in living cells (e.g. "ER-Tracker Blue-White DPX" catalogue number E12353 or "Bodipy FL C5 ceramide" catalogue number D-3521 both from Invitrogen) and antibodies that stain these structures in fixed cells, thus enabling purification of ASC by fluorescent-activated flow cytometry simply by virtue of their unusually large endoplasmic reticulum or Golgi apparatus.

Accordingly, the concentration of antibody-secreting cells in the sample can be increased by increasing the concentration of cells in the sample for cells with enlarged endoplasmic reticulum and/or Golgi apparatus as compared to control cells.

Thus, another aspect of the invention is a method of isolating an antibody-secreting cell that has a high likelihood of secreting an antibody specific for a desired antigen, comprising the steps:
 a) providing a sample from an animal that was recently immunized with the desired antigen, wherein the sample comprises a population of antibody-secreting cells that are secreting antibodies specific for the desired antigen;
 b) treating the cells in the sample with a detection agent that specifically labels the endoplasmic reticulum and/or Golgi apparatus;
 c) identifying and isolating an antibody-secreting cells, wherein high levels of endoplasmic reticulum or Golgi apparatus in the cell compared to a control is indicative of an antibody-secreting cell.

In addition, the concentration of antibody-secreting cells in the sample can be increased by increasing the concentration of cells in the sample that have high levels of intracellular immunoglobulin as compared to a control.

If a suitable preparation of antigen or a mixture of antigens is available, then these antigens can be used as the direct or indirect agent that binds to the intracellular immunoglobulins thus identifying cells secreting antibodies specific for the desired antigen.

Another aspect of the invention is a method of isolating an antibody-secreting cell that has a high likelihood of secreting an antibody specific for a desired antigen using a "reverse" hemolytic plaque assay (Gronowicz et al., 1976), comprising the steps:
 a) providing a sample from an animal that was recently immunized with the desired antigen, wherein the sample comprises a population of antibody-secreting cells that are secreting antibodies specific for the desired antigen;
 b) incubating the sample with erythrocytes coated with an agent that captures secreted antibodies in liquid or a semi-solid medium that includes, or to which is added, a source of complement and a secondary antibody that binds to and forms complexes with antibodies secreted by the antibody-secreting cells;
 c) incubating the mixture to allow hemolytic plaques to develop;
 d) identifying individual hemolytic plaques; and
 e) isolating the central single antibody-secreting cell that generated the individual hemolytic plaque.

The invention also provides methods that enable the isolation of single antibody-forming cell (AFC) that bind to a particular desired antigen from populations of cells, where such AFCs are at very low frequency and are difficult to distinguish from other cells that non-specifically bind the antigen. Therefore, methods in the invention that enable the isolation of single AFC that bind to a particular desired antigen exploit the strategy developed and validated by Townsend and colleagues to minimize the problem of non-specific binding of labeled preparations of antigen in the use flow cytometry for the enumeration of low frequency B lymphocytes that bind a particular antigen (Townsend et al., 2001). Thus, an antigen or mixture of antigens is divided into two or more parts, each of which is coupled with a different detectable agent, such as a fluorochrome. Using flow cytometry, single cells that bind proportionate amounts of the differently labelled antigens are likely to be binding the antigen specifically, can be identified and discriminated from cells that non-specifically bind either antigen preparation. Only the cells binding proportionate amounts of the differently labelled antigens and are thus likely to be binding the antigen specifically would be sorted and isolated by FACS. In the case where a suitable preparation of antigen or a mixture of antigens is available, it will be evident that the identification of specific antigen-binding cells by proportionate binding of two differentially labeled preparations of an antigen used in combination with the labeling of cells with another florescent dye, to ensure that only single cells are isolated, will provide great improvements in the efficiency of isolating monoclonal antibodies.

Accordingly, another aspect of the invention is a method of isolating an antibody-forming cell that has a high likelihood of making an antibody specific for a desired antigen comprising the steps:
 a) providing a sample from an animal that was recently immunized with the desired antigen, wherein the sample comprises a population of antibody-forming cells that are producing antibodies specific for the desired antigen;
 b) labeling the population of cells with a detection agent that facilitates the isolation of a single cell;
 c) mixing the sample with two or more parts of the desired antigen or mixtures of the desired antigens, wherein the antigens in each part are coupled to different detectable reagents that can be distinguished from one another, and
 d) isolating a single cell that binds proportionately to all of the different detectable reagents that are coupled to the antigens.

Methods are known for allowing antibody-forming cells to interact with and form conjugates with cells that exhibit an antigen that is bound specifically by the receptor on the AFC (i.e. on ABC). Thus another aspect of the invention is a method of isolating an antibody-forming cell that has a high likelihood of making an antibody specific for a desired cell surface antigen on a target cell, comprising the steps:
 a) providing a sample from an animal that was recently immunized with a target cell, wherein the sample comprises a population of antibody-forming cells that are producing antibodies specific for the desired antigen, wherein the antibodies are expressed on the surface of the antibody-forming cell;
 b) labeling the cells in the sample with a detectable reagent;
 c) labeling the target cells with a different detectable reagent;
 d) mixing the cells in the sample with the target cells and allowing the antigen-forming cells and the target cells to form cellular conjugates;
 e) isolating individual conjugates of antigen-forming cells and target cells, wherein each antigen-forming cell and target cell in the conjugate is labeled with its distinctive reagent; and
 f) isolating the antigen-forming cell from the conjugate.

Methods are also known for obtaining preparations of antigens from the membranes of a target cells. Thus, an additional aspect of the invention is a method of isolating an antibody-forming cell that has a high likelihood of producing an antibody specific for a desired cell surface antigen on a target cell, comprising the steps:
 a) providing a sample from an animal that was recently immunized with a target cell, wherein the sample comprises a population of antibody-forming cells that are producing antibodies specific for the desired antigen, wherein the antibodies are expressed on the surface of the antibody-forming cell;
 b) labeling proteins on the surface of a target cell;
 c) disrupting the target cell and isolating the labeled membrane fragments;
 d) binding aliquots of the labeled membrane fragments to differently labeled particles which can be distinguished from one another;

e) mixing the membrane fragments bound to labeled particles with cells from the sample from the animal recently immunized with the target cell; and f) isolating an antibody-forming cell that proportionately binds to all labeled particles.

It has been long known in the field that certain substances are able to directly stimulate the multiplication and differentiation of cells of the B lymphocyte lineage (and are so-called polyclonal activators of B lymphocytes). These substances include many products of microbial origin such as lipopolysaccharide (LPS) (Andersson et al., 1972; Greaves et al., 1974), and polyanioinic substances (Diamantstein et al., 1974; Ruhl et al., 1974) and flagellin (Schrader, 1973b) (Schrader, 1973a). Many of these of these, such as LPS, flagellin, RNA and CpG oligonucleotides are now known to bind to Toll-like Receptors (TLR) (Kawai & Akira, 2005). Polyanionic substances that activate B lymphocytes like dextran sulphate also bind to scavenger receptors (Acton et al., 1993) that are known to transmit stimulatory signals to cells (Asakura et al., 1999; Grewal et al., 2003) and these may account for or contribute to their stimulation of B lymphocyte multiplication and differentiation. It has been shown that signals triggered by Flagellin or LPS could synergize with signals triggered by binding of antigen to stimulate antigen-specific cells to multiply and differentiation to ASC (Schrader, 1973b; Schrader, 1973a). The ability of substances of this class to potently and directly trigger specific antibody responses in the absence of T lymphocyte help (i.e. that allowed them to act as "thymus-independent" antigens) reflected the fact that binding antigen through their antibody receptors concentrated onto the cell the signal the second signal required in addition to antigen to promote activation to multiplication and ASC formation (Schrader, 1973b). Artificial conjugates between conventional antigens or haptens and these thymus independent antigens stimulated thymus-independent generation of cells secreting antibodies specific for the hapten or antigen (Schrader, 1973b; Lange et al., 1983). Such complexes of activators of TLR and antigens such as DNA or RNA-binding proteins have been shown to result in the specific generation of ASC secreting auto-antibodies specific for DNA or RNA-binding proteins (Viglianti et al., 2003; Vollmer et al., 2005). Thus, low doses of conjugates between antigen and such thymus-independent antigens or polyclonal B lymphocyte activators, provide a way to selectively activate antigen-specific B lymphocyte (ABC) to generate ASC. Thus another aspect of the invention is a method of generating an antibody-secreting cell that has a high likelihood of making an antibody specific for a desired antigen by exploiting conjugates of antigen and polyclonal activators of B lymphocytes to focus selectively the complex of antigen and polyclonal activation specific ABC that will selectively bind the complex at low concentrations.

Accordingly, the invention includes a method of isolating an antibody-secreting cell that has a high likelihood of secreting an antibody specific for a desired antigen comprising the steps:

a) providing the isolated antibody-forming cell according to the methods of the invention;

b) inducing the differentiation of the antibody-forming cell to an antibody-secreting cell; and c) optionally, testing for a secreted antibody specific for the desired antigen.

In one embodiment, the antibody-forming cell is induced to differentiate into an antibody-secreting cell by mixing the sample with limiting amounts of a complex of the antigen bound to a Toll-like receptor ligand or other polyclonal activators of B lymphocytes.

In another embodiment, the antibody-forming cells that have been stimulated to multiply by binding the complexes of antigen and polyclonal B lymphocyte activator are allowed to form clonal colonies by culturing the cells at a low density in a semi-solid medium gelified by the addition of agents such as agarose or methyl cellulose (Kincade et al., 1976). A variety of methods can be used to confirm that ASC in a given colony are making an antibody with the desired specificity and the clone can be isolated.

The invention also includes methods of generating monoclonal antibodies specific for a desired antigen from antibody-secreting cells isolated using methods of the invention.

Accordingly, the invention provides a method of generating monoclonal antibodies specific for a desired antigen comprising the steps:

a) providing according to any of the methods of the invention an antibody-secreting cell that has a high likelihood of secreting an antibody specific for the desired antigen or a clone thereof;

b) optionally confirming that the ASC or clone thereof is making an antibody specific for a desired antigen by collecting the secreted antibody, and testing its specificity;

c) cloning nucleic acid molecules that encode the variable regions of the heavy and light chains of the antibody made by the antibody-secreting cell; and d) expressing the nucleic acid molecules that encode the variable regions or parts thereof of the heavy and light chains of the antibody made by the antibody-secreting cell.

The methods of the invention can also be used to generate libraries of monoclonal antibodies and in particular provides a way of avoiding the repeated isolation of monoclonal antibodies against the same target antigens. This is based on the ability to express the antigen-binding sites of monoclonal antibodies already generated with constant regions from another species, enabling these antibodies to be used to block binding of antibodies to the same antigens during screening of products of newly isolated ASC.

It will be evident to those skilled in the art that a variety of methods can be used to generate monoclonal antibodies from ASC isolated by the methods of this invention. These include the formation of hybridomas by fusion to a suitable cell, for example by electrofusion (Steenbakkers et al., 1993), and methods involving immortalization of ASC for example by the use of EBV for human cells or SV40 large T antigen (Pasqualini & Arap, 2004).

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIG. 2 shows the sequences of the heavy and kappa chain regions of clones E10 and D5.

DETAILED DESCRIPTION OF THE INVENTION

Figure 1:
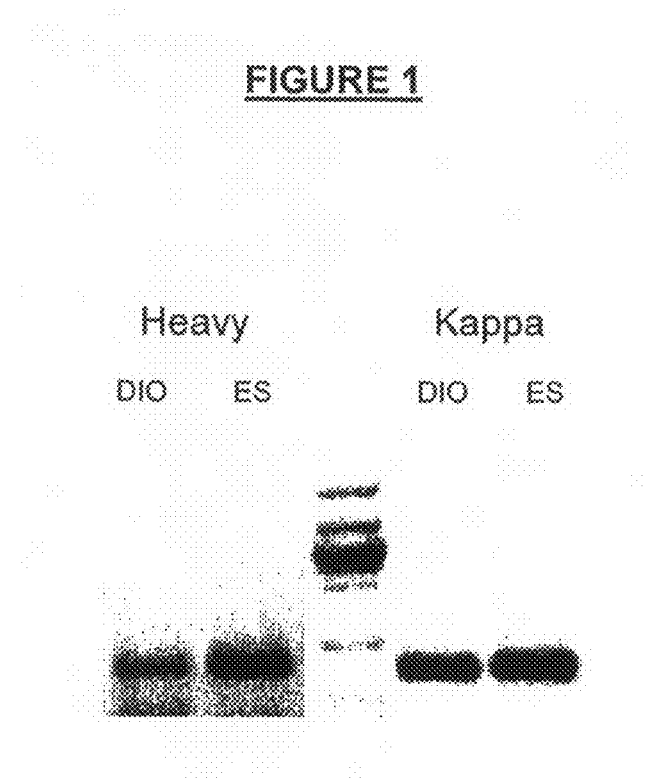
FIG. 1 shows PCR products amplified from the heavy chains ("heavy") and the light chains ("kappa") of the genes encoding the variable regions of two rabbit antibodies E5 and D10, both of which bound to a Fab fragment of human immunoglobulin MJ5.

The invention provides methods for isolating antibody-secreting cells that have a high likelihood of secreting an antibody specific for a desired antigen. In particular, the methods include processes that do not depend on the availability of a pure preparation of the desired antigen. However, this does not preclude the advantageous use of the methods of the invention with pure preparations of known antigens or mixtures thereof. The methods of the inventions enable the generation of monoclonal antibodies and libraries of monoclonal antibodies specific for a desired antigen or collection of antigens (e.g. on a cell or in a mixture).

One aspect of the invention is a method of isolating an antibody-secreting cell that has a high likelihood of secreting an antibody specific for a desired antigen, comprising the steps:
 a) providing a sample from an animal that was recently immunized with the desired antigen, wherein the sample comprises a population of antibody-secreting cells that are secreting antibodies specific for the desired antigen;
 b) increasing the concentration of antibody-secreting cells in the sample; and
 c) isolating an antibody-secreting cell.

The term "antibody-secreting cell" (ASC) as used herein means a B lineage cell that can make and secrete an antibody. The term "antibody-forming cell" (AFC) as used herein means a B-lymphocyte lineage cell that can make an antibody but does not necessarily secrete it. The term "antigen-binding cell" (ABC) means an antibody-forming cell that makes and exhibits on its surface copies of an antibody specifically binds a particular antigen, and may or may not secrete that antibody. ASC and ABC are both AFC, but not all ABC are ASC. As discussed below, in recently immunized animals, in certain tissues such as the blood, the majority of ASC bind to the antigens that have provoked the response (i.e. are specific ABC for that antigen) (Odendahl et al., 2005).

The term "high likelihood of secreting an antibody specific for a desired antigen" means the antibody-secreting cell has a reasonable probability (0.1 or greater) of secreting an antibody with specificity for a desired antigen or some component of a mixture of antigens.

The term "antigen" as used herein means any substance that is capable of stimulating the immune system in an animal. The term "antigen" includes mixtures of antigens. The invention contemplates generating antibodies to desired antigens, which can be unknown or uncharacterized. Thus, the method of the invention does not necessarily depend on knowledge of the specific antigen or on the availability of a preparation of the purified antigen. A mixture that includes the desired, yet possibly unknown antigen or antigens, including a cell or population of cells, can be used to confirm that an antibody-secreting cell (or clone of antibody-secreting cells) that has a high likelihood of secreting an antibody specific for the desired antigen indeed secretes an antibody against a desired antigen. As described, a mixture that includes the desired yet possibly unknown antigen, including a cell or population of cells, can also be used to isolate antibody-forming cells and generate clones of antibody-secreting cells that have a high likelihood of secreting an antibody specific for the desired antigens.

As used herein, the term "animal" includes all members of the animal kingdom that can produce antibodies, preferably humans.

The invention contemplates immunizing and re-immunizing an animal against a desired antigen or mixture of antigens. The animal may be immunized and re-immunized by standard methods known to persons skilled in the art. For example, the animal may be immunized by intravenous injection or intramuscular injection with a substance that contains the desired antigens, which may be unknown or uncharacterized. The substance is typically administered together with an adjuvant, using practices known to those skilled in the art. Preferably, the immunization method avoids the use of adjuvants that provoke an immune response against themselves. If the use of such an adjuvant is necessary for the initial immunization, it is preferable to avoid the use of such an agent when re-immunizing or boosting with the antigen. In addition, immunization can occur as a result of an infection with a microorganism, either naturally acquired or artificially acquired. Immunization also can be the result of a growth of a cancer or allergic or autoimmune disease or a result of pregnancy. A distinguishing feature of most of the methods of the invention is that they exploit the fact that, consequent upon immunization, ASC that are secreting antibodies specific for the immunizing antigens enter the blood in large numbers (Barington et al., 1990b; Heilmann et al., 1987; Heilmann & Pedersen, 1986; Thomson & Harris, 1977; Bernasconi et al., 2002; Odendahl et al., 2005). As noted, these ASC also bind the immunizing antigen(s) through surface receptors (Odendahl et al., 2005)). Importantly these ASC that are secreting antibodies specific for the immunizing antigens make up a large fraction of antibody-secreting cells that are present in the blood shortly after re-immunization with a particular antigen or mixture of antigens. For example, in humans immunized with pneumococcal polysaccharides, at 6-9 days after immunization, 20-80% of ASC in the blood are making antibodies specific for pneumococcal polysaccharides (Heilmann & Pedersen, 1986). Likewise in humans re-immunized with tetanus toxoid, a large fraction of ASC in the blood at days 6-8 are secreting antibodies specific for tetanus toxoid (Bernasconi et al., 2002; Odendahl et al., 2005). ASC in the blood are distinguished from B lymphocytes by lower expression of CD19 and high expression of CD27 and CD38 (Odendahl et al., 2005), lack of expression of CD20 (Horst et al., 2002) and in most cases expression of CD138 (Sanderson et al., 1989)(Horst et al., 2002). Moreover, differential expression of the cell-surface markers HLA-DR, CD38 and CXCR3 and CXCR4 can be used to identify a subpopulation of these AFC in which the vast majority of ASC are making antibodies specific to the antigen used for re-immunization (Odendahl et al., 2005). CD138 is also present on antigen-specific ASC that increase in number in the blood after re-immunization of humans (see Horst et al., 2002). Thus in the case of humans, methods are available that provide means of obtaining from the blood of an individual undergoing an active immune response to an antigen, a population of ASC, most of which are making antibodies specific for antigens involved in the ongoing immune response. Thus, the animal is preferably re-immunized or boosted, and then samples of blood are taken a short time later, usually 4-8 days, preferably 6 days.

As used herein, the term "recently immunized" means that the animal was exposed to an initial or subsequent contact with an antigen or antigens in the previous 4-8 days and is undergoing an active immune response that results in the generation of new ASC and their entry to the blood. The interval after the initiation of an immune response at which the numbers and frequency of ASC in the blood that are making antibodies specific for the immunizing antigen(s) peak, varies somewhat depending on the circumstances, but usually is from 6-8 days after immunization. It can however readily be ascertained empirically by measuring the frequency of ASC by simple methods (Odendahl et al., 2004; Horst et al., 2002; Manz et al., 1995) as the number of ASC making antibodies specific for the immunizing antigens correlates tightly with the total number of ASC eg (Odendahl et al., 2004). The term "recently immunized" also encompasses situations where antigen or antigens persist in the body because of continuous exposure (e.g. to allergens), or as components of persisting infectious agents or the body itself and the active immune response is thus ongoing. It is known that this ongoing immune response also results in a high proportion of the ASC in the blood making antibodies specific for the persisting antigen(s) (Horst et al., 2002).

The term "sample" as used herein refers to a sample of tissue from an animal immunized, preferably recently immunized, with an antigen or mixture of antigens that contains antibody-forming cells or, in a preferred embodiment, naturally contains a population of antibody-secreting cells in which a high proportion of the cells are secreting antibodies specific for the desired antigen or mixture of desired antigens involved in the immune response. Such a preferred sample of a bodily fluid or tissue that naturally contains a population of antibody-secreting cells in which a majority of these cells are secreting antibodies specific for the desired antigen or mixture of desired antigens involved in the immune response can be obtained from but is not limited to blood, lymphatic fluid, lymph nodes or collections of lymphoid tissue from the animal, usually soon after it has been re-immunized with the antigen or mixture of antigens or during an ongoing immune response. For example, the sample could include tissue from the site of a pathological process at which there was an active ongoing immune response. The blood however is a preferred source because it is greatly enriched in ASC that produce antibodies specific for the immunizing antigen at certain times after immunization, and because of its convenience—especially in humans—enabling repeated sampling over several days of an active immune response. This ensures that the peak frequencies of specific ASC are exploited and the number of ASC harvested maximized.

In one embodiment, the antibody-secreting cells are identified and isolated using a characteristic set of antigens known to be expressed on their cell surface. Specifically, in humans, antibody-secreting cells likely to be secreting antibodies against antigens against which there is an ongoing immune response, are known to express high levels of antigens such as CD38, CD27, CD138 and HLA-DR, but low levels of CD20, CXCR3 and CXCR4 (Odendahl et al., 2005). Thus, the concentration of antibody-secreting cells in the sample can be increased using selection for or against surface markers on the antibody-secreting cells. For example, the sample can be enriched for cells expressing high levels of CD27, CD38, CD138 and/or HLA-DR but low levels of CXCR3, CXCR4 and/or CD20 (Odendahl et al., 2005). Odendahl and colleagues concluded that the vast majority of $CD19^{low}/CD27^{high}/HLADR^{high}$ ASC expressed antibodies specific for the immunizing antigens. They noted that this agreed with the results of Bernasconi et al. (Bernasconi et al., 2002) who also enumerated a very large but transient increase in the frequency of ASC specific for the immunizing antigen in the blood around 6 days after re-immunization. Thus using flow cytometry it is possible to use a variety of cell-surface markers to select for newly generated human ASC making antibodies specific for the immunizing antigen(s) and select against that fraction of ASC that enter the blood after immunization because they have been displaced by the newly generated ASC from niches (e.g. in the bone marrow) and are not making antibodies against the immunizing antigen and that are characterized by the expression of low levels of HLA DR, lower levels of CD38 and high levels of CXCR3 and CXCR4 (Odendahl et al., 2005).

It is useful in cases where it is not desired to obtain an antibody of the IgA class to negatively select against cells with IgA on their surface. This is because many of the "background" ASC present in the blood that are not making antibodies specific for an ongoing immune response to intramuscularly injected antigens, are making IgA antibodies (Odendahl et al., 2004) and are presumably involved in an ongoing response to antigens at mucosal surfaces.

A person skilled in the art will appreciate that different methods may be used to enrich for cells expressing high levels of CD27, CD38, CD138 and/or HLA-DR and/or deplete cells expressing high levels of CXCR3, CXCR4 and/or CD20 cells, including a fluorescence-activated cell sorter and magnetic beads.

Another well-known characteristic of antibody-secreting cells is that they are distinguished from other blood or lymphohemopoietic cells by gross enlargement of their endoplasmic reticulum and of their Golgi apparatus. Moreover, there are commercially available fluorescent dyes that stain the endoplasmic reticulum or Golgi apparatus in living and fixed cells (e.g. "ER-Tracker Blue-White DPX" or "Bodipy FL C5 ceramide", both from Invitrogen) and thus enable purification or enrichment of ASC by fluorescent-activated flow cytometry by virtue of their unusually large endoplasmic reticulum or Golgi apparatus. In addition, antibody-secreting cells can be distinguished from other blood or lymphohemopoietic cells, because the cells contain high levels of intracellular immunoglobulin.

Accordingly, the concentration of antibody-secreting cells in a sample can be increased by increasing the concentration of cells in the samples with enlarged endoplasmic reticulum and/or Golgi apparatus as compared to control cells. In another embodiment, the concentration of antibody-secreting cells in the sample is increased by increasing the concentration of cells in the sample that have high levels of intracellular immunoglobulin as compared to Control cells. The term "control" cells as used here refers to cells that are known to be non-antibody producing or forming cells, particularly non-antibody-secreting cells.

Yet another aspect of the invention is a method of isolating an antibody-secreting cell that has a high likelihood of secreting an antibody specific for a desired antigen, comprising the steps:

a) providing a sample from an animal that was recently immunized with the desired antigen, wherein the sample comprises a population of antibody-secreting cells that are secreting antibodies specific for the desired antigen;

b) treating the cells with a fixative that prevents the degradation or loss of nucleic acids from the cells, the effects of which can be reversed, and then permeabilizing the cells;

c) treating the cells with a detection agent that directly or indirectly recognize immunoglobulins inside the permeabilized cell;

d) identifying and isolating an antibody-secreting cell, wherein high levels of intracellular immunoglobulin compared to a control is indicative of an antibody-secreting cell and e) Reversing the cross-linking effects of the fixative.

One convenient fixative is formaldehyde as the cross-linking it causes is reversed by heating (Vasilescu et al., 2004).

A person skilled in the art will recognize that the described methods of increasing the concentration of antibody-secreting cells in the sample can be exploited alone or in combination with other methods.

The invention contemplates isolating a single antibody-secreting cell or a clone of antibody-secreting cells all of which are producing an identical antibody. The use of more than one antibody-forming cell (unless all antibody-forming cells are members of the same clone and are making the same antibody) to amplify and copy and clone the genetic information encoding the antigen-binding region of the desired antibody will result in inefficiencies in subsequent steps to generate monoclonal antibodies. For instance, if the nucleic acids that encode the variable regions of the heavy and light chains of the antibody made by the antibody-secreting cells are amplified and copied from two antibody-secreting cells that are secreting different antibodies, then two sets of heavy chain variable region nucleic acids and two sets of light antibody nucleic acids would be recovered. This would require additional work to determine which heavy chain was originally matched with which light chain to generate the desired antibody. Thus, for reasons of efficiency it is important to isolate a single antibody-secreting cell or clone thereof, which will be used in later steps to generate a monoclonal antibody that has specificity for a desired antigen.

Therefore, one embodiment of the invention uses a label that enables single cells to be distinguished from multiple cells to ensure the isolation of a single antibody-secreting cell or antibody-forming cell from a sample. For example, cells in the sample containing the antibody-secreting cells can be labeled with a fluorescent compound that fluoresces at a wavelength that is distinct from other labels used to identify antibody-secreting cells. Thus single cells can be distinguished from multiple cells by fluorometric quantification of the amount of fluorescence and fluorescent microscopy can be used to visually confirm that a single cell is isolated. The dye should be a vital one allowing subsequent culture and expansion of the cell. A convenient dye is Hoescht 33342 however a person skilled in the art will appreciate that other dyes can be used, for example fluorescent dyes which stain proteins in cells, such as carboxy-fluorescein diacetate, succinimidyl ester (CFSE), or fluorescent dyes which integrate in membranes, such as PKH26.

In another embodiment, single antibody-secreting cells can be isolated using limiting dilution. For example, plating cells at a dilution of an average of 0.2 cells per well will ensure that most individual wells that contain a cell, contain only one cell. As described the use of fluorescent labels and fluorescent microscopy facilitates visual confirmation that a single cell has been isolated.

Single antibody-secreting cells can also be isolated using micromanipulation (Nossal et al., 1968).

Another embodiment of the invention is the use of methods that capture antibodies that the cell has secreted on the surface of that cell, to increase the concentration of antibody-secreting cells in a sample from an animal immunized against a desired antigen. Such methods have been described in the literature for example by Manz and colleagues (Manz et al., 1995) and have been used to isolate ASC, for example from mice (Manz et al., 1997), from human blood (Horst et al., 2002) and from mixtures of cells (Carroll & Al-Rubeai, 2005).

For example, particles, beads or other substances that can be attached to the surface of a cell are coated with a reagent that captures antibodies of the desired class are used. The reagent could be protein A or antibodies that recognize IgG in order to capture IgG antibodies. The particles, beads or other substances are selected for physical properties such as charge that cause them to adhere to cells, or are coupled with reagents such as antibodies or a lectin, such as phytohemagglutinin, that adheres them to cells. The sample from the immunized animal is mixed with the particles, beads or other substances. For instance, the sample is gently agitated with the particles, beads or other substances for 30 minutes at room temperature to allow the beads to adhere to the cells. The cells with bound particles, beads or other substances may be separated from unbound beads by centrifugation. The cells with bound particles, beads or other substances can then be incubated at 37° C. in a suitable medium, which may include a gelifying agent to slow diffusion of the secreted antibodies and confine them to the vicinity of the cell that secreted them as described by Manz and (Manz et al., 1995) for a short time (e.g. 30 minutes). Antibodies of the desired class that are secreted by the antibody secreting cells will bind to the beads attached to their surface. The cells that are decorated by the binding of the antibodies they have secreted to the beads can be easily identified and isolated, for instance by FACS or by magnetic fields (Horst et al., 2002). A person skilled in the art will appreciate that a mixture of antigens or fragments of cell membranes can be coupled to the particles or beads to act as the agent that captures antibodies secreted by the cell to which the particle is bound.

Accordingly, another aspect of the invention is a method of isolating an antibody-secreting cell that has a high likelihood of secreting an antibody specific for a desired antigen, comprising the steps:

a) providing a sample from an animal that was recently immunized with the desired antigen, wherein the sample comprises a population of antibody-secreting cells that are secreting antibodies specific for the desired antigen;

b) allowing cells in the sample to adhere to particles that are coated with an agent that captures antibodies secreted by the individual cells, such as Protein A or Protein G, or antibodies that bind to antibodies from the species of animal from which the sample was obtained; and c) identifying and isolating an antibody-secreting cell by detection of the captured antibodies using detectable reagents.

It will be appreciated by those skilled in the art that if available in suitable form, preparations of antigen can also be used as agents to capture antibodies secreted by ASC or as agents to identify those antibody-secreting cells which are secreting and to which are bound captured antibodies specific for the antigen.

The invention exploits a modification of the reverse hemolytic plaque assay (Gronowicz et al., 1976) to isolate an antibody-secreting cell that has a high likelihood of secreting an antibody specific for a desired antigen. For example, a sample from a recently immunized animal that naturally contains a population of antibody-secreting cells in which a high proportion of the cells are secreting antibodies specific for the desired antigen or mixture of desired antigens that stimulated the ongoing immune response is mixed with indicator erythrocytes (e.g. from a sheep) that are coated with Protein A or G or antibodies that bind to antibodies of the species of animal from which the antibody-secreting cell to be isolated are derived. Antibodies secreted by the antibody-secreting cell will bind to secondary antibodies that are specific for immunoglobulins of the species of the ASC and the complexes bind to the indicator erythrocytes in the vicinity of the ASC. Because of the presence of complement this leads to the lysis of the erythrocytes in the vicinity of the ASC and the formation of a clearing or "plaque". At the centre of each plaque is the antibody-secreting cell whose secreted antibodies generated it and this central ASC can be readily isolated by micromanipulation (Nossal et al., 1968; Schrader & Nossal, 1974).

Accordingly, the invention includes a method of isolating an antibody-secreting cell that has a high likelihood of secreting an antibody specific for a desired antigen using a reverse plaque assay, comprising the steps:
  a) providing a sample from an animal that was recently immunized with the desired antigen, wherein the sample comprises a population of antibody-secreting cells that are secreting antibodies specific for the desired antigen;
  b) incubating the sample with erythrocytes coated with an agent that captures secreted antibodies in liquid or a semi-solid medium that includes, or to which is added, a source of complement and a secondary antibody that binds to and forms complexes with antibodies secreted by the antibody-secreting cells;
  c) incubating the mixture to allow hemolytic plaques to develop;
  d) identifying individual hemolytic plaques; and
  e) isolating the central single antibody-secreting cell that generated the individual hemolytic plaque.

There are many methods known to those skilled in the art for the identification of AFC that are making antibodies specific for a particular antigen that depend on labeling the antigen with a detectable agent and detecting its binding to the surface of the cell (i.e. detecting ABC).

A detectable reagent or agent as used herein means any reagent that is capable of producing, either directly or indirectly, a detectable signal. For example, the detectable reagent may be radio-opaque or a radioisotope, such as $^{3}$H, $^{14}$C, $^{32}$P, $^{35}$S, $^{123}$I, $^{125}$I, $^{131}$I; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion.

The desired antigen or mixture of antigens can be coupled to a detectable reagent by methods known to persons skilled in the art. For example, reagents can be coupled to the antigen through functional groups on each molecule or conjugating agents can be used such as glutaraldeydes, imidates and N-hydroxysuccinimidyl esters.

It is well-known to those skilled in the art that labeled antigens interact non-specifically with cells of the immune system for reasons that are not well-understood (discussed in Townsend et al (Townsend et al., 2001)). Thus, because the frequency of B lymphocytes that bind a particular antigen are characteristically very low, they are hard to distinguish from the cells that bind the antigen non-specifically and that do not make antibodies specific for that antigen. Therefore in the present invention, to decrease the frequency with which cells that exhibit non-specific binding of antigen are isolated, the cell population is mixed with pre-optimized amounts of two, differently labeled aliquots of the preparation of antigen. Single cells that exhibit coincident, proportional binding of both labeled preparations are highly likely to exhibit specific receptors for the antigen as shown by Townsend and colleagues (Townsend et al., 2001). Methods of the invention thus use two or more aliquots of the desired antigen or mixture of antigens that are labeled with different detectable reagents and mix them in preoptimized ratios with the cell population containing the antibody-forming cells it is desired to isolate. Only cells that bind proportionately to the differently labeled aliquots of antigen are likely to be specific binders and are isolated. For example, the two portions of antigen or mixture of antigens can be coupled to two different fluorochromes that fluoresce at different wavelengths. Specific antibody-forming cells are identified as only those cells that exhibit proportionate binding to both preparations of antigens (Townsend et al., 2001). These specific antibody-forming cells can then be sorted into single wells by FACS. As noted by Townsend, more than two labels can be used to diminish further the chance that binding is non-specific. In another variant of this strategy, one aliquot of the antigen preparation can be attached to a magnetic particle and the other to a fluorochrome and after exposing the cell population to a mixture of the aliquots, the cell population can be sequentially subjected to magnetic enrichment of cells binding the antigen followed by purification of cells binding the fluorochrome-labelled antigen preparation using FACS.

Accordingly, another aspect of the invention is a method of isolating an antibody-forming cell that has a high likelihood of making an antibody specific for a desired antigen comprising the steps:
  a) providing a sample from an animal that was recently immunized with the desired antigen, wherein the sample comprises a population of antibody-forming cells that are producing antibodies specific for the desired antigen;
  b) labeling the population of cells with a detection agent that facilitates the isolation of a single cell;
  c) mixing the sample with two or more parts of the desired antigen or mixtures of the desired antigens, wherein the antigens in each part are coupled to different detectable reagents that can be distinguished from one another, and
  d) isolating a single cell that binds proportionately to all of the different detectable reagents that are coupled to the antigens.

In a case where the antigens against which it is desired to generate monoclonal antibodies are present on the surface of cells, the invention exploits well-known methods for forming and identifying conjugates of the target cell and an antibody-forming cell exhibiting an antibody receptor specific for an antigen on its surface.

Another aspect of the invention is a method of isolating antibody-forming cells that have a high likelihood of making an antibody specific for a desired cell surface antigen on a target cell, comprising the steps:
  a) providing a sample from an animal that was recently immunized with a target cell, wherein the sample comprises a population of antibody-forming cells that are producing antibodies specific for the desired antigen, wherein the antibodies are expressed on the surface of the antibody-forming cell;
  b) labeling the cells in the sample with a detectable reagent;
  c) labeling the target cells with a different detectable reagent;
  d) mixing the cells in the sample with the target cells and allowing the antigen-forming cells and the target cells to form cellular conjugates;
  e) isolating individual conjugates of antigen-forming cells and target cells, wherein each antigen-forming cell and target cell in the conjugate is labeled with its distinctive, reagent; and
  f) isolating the antigen-forming cell from the conjugate.

The phrase "isolating individual conjugates of antibody-forming cells and target cells" as used herein means that a single labeled target cell and a single AFC labeled with a different reagent are isolated together. For example, if the AFC and target cells are labeled with different fluorochromes, FACS can be used to isolate a conjugate of two cells, in which each cell is labeled with a different fluorochrome.

There are known methods for preparing fragments of cellular membranes and labeling them or coupling them to labeled particles. Therefore an additional aspect of the invention is the exploitation of these methods to isolate single antibody-forming cells that have a high likelihood of secreting an antibody specific for a desired cell surface antigen on a target cell, comprising the steps:
  a) providing a sample from an animal that was recently immunized with a target cell, wherein the sample comprises a population of antibody-forming cells that are producing antibodies specific for the desired antigen, wherein the antibodies are expressed on the surface of the antibody-forming cell;
  b) labeling proteins on the surface of a target cell;
  c) disrupting the target cell and isolating the labeled membrane fragments;
  d) binding aliquots of the labeled membrane fragments to differently labeled particles which can be distinguished from one another
  e) mixing the membrane fragments bound to labeled particles with cells from the sample from the animal recently immunized with the target cell; and
  f) isolating an antibody-forming cell that proportionately binds to all labeled particles.

The proteins on the surface of the target cell can be labeled with any detectable reagent disclosed above. For example, the proteins on the outer surface of the target cell can be labeled by coupling them with biotin by reaction with free amines. The labeled target cells can be disrupted by sonication to generate labeled membrane fragments and the biotinylated proteins bound to fluorochrome-coupled avidin or streptavidin in solution or on particles. To decrease the frequency with which false positives are identified due to non-specific binding of antigen to cells other than antibody-forming cells in the population (discussed in Townsend et al (Townsend et al., 2001)), the cell population is mixed with predetermined amounts of two aliquots of the preparation of antigen, each labeled differently, for example one bound to fluorescein-coupled avidin and the other to APC-coupled streptavidin. Coincident, proportional binding of the two labeled preparations of antigens to a cell makes it highly likely that the observed binding is specific. This principle has been described in detail and validated by Townsend and colleagues for the purpose of accurately enumerating low-frequency antigen-binding cells (Townsend et al., 2001). Using flow cytometry, specific antibody-forming cells can be isolated in single wells for further culture. Thus, the labeled membrane fragments are bound to two different particles, such as beads, which can be distinguished from one another. For example, the particles may fluoresce at different wavelength from one another or be of different size, such that they can be differentiated by FACS. The particle-bound labeled membrane fragments are mixed with B cells from an animal immunized with the target cell. B cells that secrete antibodies specific for an antigen on the labeled membrane can be recognized by coincident binding of both types of particles.

Another aspect of the invention is a method of artificially generating a population of antibody-secreting cells, members of which have a high likelihood of making an antibody specific for a desired antigen comprising the steps:
  a) providing an antibody-forming cell according to any one of the methods of the invention, such as a memory B lymphocytes;
  b) inducing the differentiation of the antibody-forming cell to an antibody-secreting cell; and
  c) optionally, testing for a secreted antibody specific for the desired antigen.

In one embodiment, the antibody-forming cell is induced to differentiate into an antibody-secreting cell by mixing the sample with limiting amounts of a complex of the antigen bound to a Toll-like receptor ligand or other polyclonal activators of B lymphocytes.

In another embodiment, clonal colonies derived from AFC's are isolated by culturing the AFC's at a low cell-density in a semi-solid medium gelified by the addition of agents such as agarose or methyl cellulose. It is critical that these gelifying agents are not themselves contaminated with substances such as TLR ligands or other polyclonal activators of B cells as has been demonstrated to be the case with agar (Kincade et al., 1976). Nor should TLR ligands or other polyclonal activators of B cells contaminate the tissue culture medium or the serum. Thus in the absence of the complex of antigen and the TLR ligand and/or the polyclonal B-lymphocyte activator, there should be no proliferation or differentiation of the AFC. Under these conditions, with the presence of limiting amounts of the complex of antigen and the TLR ligand and/or the polyclonal B-lymphocyte activator insufficient to stimulate AFC that are not specific for the antigen, only those AFC cells that bind the antigen associated with the TLR ligand and/or the polyclonal B-lymphocyte activator and thus concentrate the TLR ligand or the polyclonal B-lymphocyte activator onto their surface will be stimulated to multiply and differentiate (Lange et al., 1983; Schrader, 1973b) and will develop into isolated clonal colonies of ASC. Moreover the combination of signals from the antigen receptor and TLR renders B lymphocytes susceptible to stimulatory factors from activated T lymphocytes. Thus in the presence of limiting amounts of the complexes of antigens and the TLR-ligand and activators, only those B lymphocytes that have high-affinity antibody-receptors for the desired antigen will concentrate these complexes at their surface and be activated and become susceptible to activation by molecules secreted from T lymphocytes (Schrader, 1973a). Thus in the method, memory B lymphocytes are cultured with limiting amounts of the complexes of TLR-ligand and antigens that do not stimulate the proliferation and differentiation to ASC of non-antigen specific B lymphocytes and with supernatants of cultures of T lymphocytes that have been stimulated by allogeneic interactions (Schrader, 1973a), or mixtures of cytokines such as IL-2, IL-10, IL-6 and IL-15 and IL-21.

Toll-like receptor ligand as used herein refers to pathogen-associated microbial patterns that bind to toll-like receptors (Kawai & Akira, 2005). Toll-like receptor ligands include various bacterial cell wall components, such as lipopolysaccharide, peptidoglycan and lipopeptides, as well as flagellin, bacterial DNA, containing unmethylated CpG di-nucleotides, and viral double-stranded and single-stranded RNA (Schrader, 1973b). Anionic polymers that stimulate B cell differentiation to antibody-secreting cells include without being limiting dextran sulphate and poly I:C (Diamantstein et al., 1974; Ruhl et al., 1974).

In one embodiment, antigen or a mixture of antigens is coupled to TLR ligands such as LPS, CpG, peptidoglycan, or flagellin or to other substances that stimulate the differentiation of B lymphocytes of the relevant species to antibody secreting cells such as anionic polymers, like dextran sulphate using chemistry known to those skilled in the art. For example, TLR ligands such as CpG or dextran sulphate can be coupled to the antigen through functional groups on each molecule using conjugating agents such as glutaraldeydes, imidates and N-hydroxysuccinimidyl esters. Preferably a mixture of stimulatory conjugates of the antigens and different classes of polyclonal activators (e.g. those acting through TLR and those through other receptors) is used such as with antigen complexed with LPS and antigen complexed with dextran sulphate. It is important to use low doses of the conjugates so that only those AFC (such as memory B cells) with immunoglobulin receptors specific for the antigen will bind and concentrate sufficient amounts of the TLR ligand or other B lymphocyte activators to stimulate differentiation to antibody-secreting cells.

Clones of the isolated antibody-secreting cells and isolated antibody-forming cells can be generated by methods known to persons skilled in the art. For example, the isolated antibody-secreting cells or isolated antibody-forming cells can be stimulated to expand into a clone of cells enabling detailed testing of the specificity and efficacy of the antibody produced by the clone. Thus ABC or ASC that have been isolated by flow cytometry can be plated in wells containing strictly one cell per well as described and expanded to clones of ASC using methods known to those skilled in the art as exemplified by the work of Zeubler (Wen et al., 1987) and involving culture with activated T lymphocytes such as the murine lymphoma EL4 (Wen et al., 1987), or other T lymphomas, if possible originating from the same species as the ABC or ASC. CD40L ideally of the same species as the ABC or ASC is also useful to add, ideally in a membrane-bound form. Also added are supernatants of cultures of activated T lymphocytes of the same species of origin as the ABC or ASC. These can be activated for example by stimulation with the phorbot ester TPA and the co-culture of allogeneic lymphocytes from outbred individuals of the species. Also added are ligands for toll-like receptors (TLR) such as Staphylococci Cowan Strain A, flagellin, endotoxin or CpG oligonucleotides that stimulate B lymphocytes of the species in question to multiply and differentiate to ASC(Schrader, 1973b), (Bernasconi et al., 2002; Schrader, 1973a) together with soluble factors like interleukins and cytokines such as IL-2, IL-4, IL-6, IL-10, IL-15 and IL-21 (Ettinger et al., 2005; Kindler et al., 1995; Ozaki et al., 2004; Vernino et al., 1992) known to those skilled in the art.

Clones are expanded for periods of typically 6 or up to 10 days and supernatants are tested for the presence of immunoglobulin using methods such as ELISA. Using methods well-known to those versed in the art, the antibodies produced by these individual clones are assessed for their ability to bind to the immunizing cell or to an antigen or to the components of the immunizing mixture.

Alternatively, as a means of expanding clones of antibody-secreting cells from individual antibody-forming cells or antibody-secreting cells, instead of plating single cells in individual cultures, multiple selected ABC or ASC are plated at low density (such as 10-200 cells per ml) in a single culture in a tissue-culture medium that is semi-solid on account of the incorporation into the medium of agents such as methylcellulose or agar or agarose so that when single cells expand to clones, these clones grow as colonies of cells that, because the cells are contained in their movement by the semi-solid nature of the medium are each physically separated from one another (Kincade et al., 1976). Into this medium is incorporated the same stimulatory TLR ligands and cytokines such as IL-2, IL-10, IL-6 and IL-21 known to those skilled in the art. Also useful is the inclusion in the cultures, of a layer of irradiated, typically adherent feeder cells (e.g. fibroblasts (Nossal & Schrader, 1975)) that are on the bottom of the culture dish or are suspended in another layer of semisolid medium, beneath the semisolid medium in which the ABC or ASC are included.

When the colonies (that is clones) of cells have grown to detectable size, these colonies are transferred into individual cultures for collection and testing of the antibodies secreted by the clone. Alternatively the layer of gelified medium can be overlayed with a membrane such as a nitrocellulose membrane to which is coupled an agent to capture antibody such as protein A or G or an antibody that binds antibodies from the same species as the antibody-forming cells, or a mixture of antigens. This permits the antibodies secreted by individual colonies to be captured by the adjacent area of the membrane. By marking the culture dish and the membrane, areas of the membrane where binding of the desired antibody is detected, can be subsequently correlated with the location of the corresponding colonies in the medium. Those areas of the membrane that have bound antibodies that are specific for the desired antigens can be identified by methods known to those skilled in the art for example by detecting binding of labeled antigen or labeled antigen from a labeled mixture of antigens (e.g. antigen or a mixture of antigens conjugated with biotin and detected using fluorochrome-labelled streptavidin) or detectable particles coupled with the mixture of antigens or antigen in the case where antibodies have been captured by general means or in the case where antibodies have been captured by binding to mixtures of antigens or antigen, by labeled agents that detect binding of antibody. Colonies that are secreting antibodies against the desired antigens can be located by comparison with the areas located on the membrane and the cells can be isolated by micromanipulation. In another embodiment a surface or membrane is placed adjacent to the semi-solid medium and an agent is coupled to the surface or membrane that captures antibodies secreted by the cells, such as Protein A or Protein G, or antibodies that bind to antibodies from the same species of animal from which the sample was obtained, or antigen or a mixture of antigens, to identify colonies of antibody-secreting cells. In a preferred embodiment a nitrocellulose membrane is used.

The single ASC isolated by the methods of the invention can also be cultured to allow collection and detailed testing of secreted antibodies. For example, single ASC may be plated in the well of a suitable micro-culture system (such as a "Terasaki" plate) in a small volume (5 microliters) of tissue-culture medium, eg RPMI 1640 or Dulbecco's Modified Eagle's Medium supplemented with 2 mercapto-ethanol ($5 \times 10^{-4}$ M). To optimize survival, there should be present filler cells such as 3T3 fibroblasts, stromal cells such as OP/9, or dendritic cells or macrophages, ideally from the same species as the ASC. These provide metabolic support and also cytokines known to those skilled in the art such as IL-2, IL-6, IL-10, IL-15, IL-21 and SDF-1 (Cassese et al., 2003) which can also be added to the medium. When incubated under these conditions, individual ASC will produce useful amounts of antibodies which can be collected and tested for their binding properties.

The invention also includes methods of generating monoclonal antibodies specific for a desired antigen from antibody-secreted cells isolated using methods of the invention. Methods of the invention can also be used to generate libraries of monoclonal antibodies.

Accordingly, the invention provides a method of generating monoclonal antibodies specific for a desired antigen comprising the steps:

a) providing according to any of the methods of the invention an antibody-secreting cell that has a high likelihood of secreting an antibody specific for the desired antigen;

b) optionally confirming that the ASC or clone thereof is making an antibody specific for a desired antigen by collecting the secreted antibody and testing its specificity;

c) cloning nucleic acid molecules that encode the variable regions of the heavy and light chains of the antibody made by the antibody-secreting cell; and d) expressing the nucleic acid molecules that encode the variable regions or parts thereof of the heavy and light chains of the antibody made by the antibody-secreting cell.

There are a variety of strategies well-known to those skilled in the art which enable copying of the required genetic information from single cells or clones of cells derived from clonal expansion of single cells. These include copying information from genomic DNA in ASC (Kuppers et al., 1993) or, as ASC produce relatively large amounts of mRNA that encode the antibody they produce, making sand amplifying cDNA corresponding to this mRNA (Babcook et al., 1996; Coronella et al., 2000; Lagerkvist et al., 1995; Wang & Stollar, 2000; Weitkamp et al., 2003; U.S. Pat. No. 5,627,052 (1997) Schrader, J. W.).

The term "monoclonal antibodies" as used herein is intended to include Fab, Fab', F(ab')$_2$, scFv, dsFv, ds-scFv, dimers, minibodies, diabodies, and multimers of the generated antibody. Antibodies can be fragmented using conventional techniques. For example, F(ab')$_2$ fragments can be generated by treating the antibody with pepsin. The resulting F(ab')$_2$ fragment can be treated to reduce disulfide bridges to produce Fab' fragments. Papain digestion can lead to the formation of Fab fragments. Fab, Fab' and F(ab')$_2$, scFv, dsFv, ds-scFv, dimers, minibodies, diabodies, bispecific antibody fragments and other fragments can also be synthesized by recombinant techniques.

Nucleic acid molecules encoding the variable regions of the heavy and light chains of the antibody made by the antibody-secreting cell can be cloned using techniques known to persons skilled in the art. For example, genomic DNA from the isolated antibody-secreting cell can be isolated and analyzed or mRNA expressed by the isolated antibody-secreting cell can be made into cDNA and then isolated and analyzed.

A person skilled in the art will appreciate that nucleic acid molecules encoding the variable regions of the heavy and light chains of the antibody made by the antibody-secreting cells can be expressed using techniques know to persons skilled in the art.

Accordingly, the nucleic acid molecules of the present invention may be incorporated in a known manner into an appropriate expression vector which ensures good expression of the heavy and light chains of an antibody. Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", which means that the expression vectors contain a nucleic acid molecule of the invention and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

Suitable regulatory sequences may be derived from a variety of sources, including bacterial, fungal, viral, mammalian, or insect genes (For example, see the regulatory sequences described in Goeddel, Gene Expression Technology Methods in Enzymology 185, Academic Press, San Diego, Calif. (1990)). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

Recombinant expression vectors can be introduced into host cells to produce a transformed host cell. The terms "transformed with", "transfected with", "transformation" and "transfection" are intended to encompass introduction of nucleic acid (e.g. a vector) into a cell by one of many possible techniques known in the art. The term "transformed host cell" as used herein is intended to also include cells capable of glycosylation that have been transformed with a recombinant expression vector of the invention. Prokaryotic cells can be transformed with nucleic acid by, for example, electroporation or calcium-chloride mediated transformation. For example, nucleic acid can be introduced into mammalian cells via conventional techniques such as calcium phosphate or calcium chloride co-precipitation, DEAE-dextran mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

Suitable host cells include a wide variety of eukaryotic host cells and prokaryotic cells. For example, the proteins of the invention may be expressed in yeast cells or mammalian cells. Other suitable host cells can be found in Goeddel, Gene Expression Technology: Methods in Enzymology 185, Academic Press, San Diego, Calif. (1991). In addition, the heavy and light chains of the antibody may be expressed in prokaryotic cells, such as *Escherichia coli* (Zhang et al., Science 303(5656): 371-3 (2004)).

Yeast and fungi host cells suitable for carrying out the present invention include, but are not limited to *Saccharomyces cerevisiae*, the genera *Pichia* or *Kluyveromyces* and various species of the genus *Aspergillus*. Examples of vectors for expression in yeast *S. cerevisiae* include pYepSec1 (Baldari et al., Embo J. 6:229-234 (1987)), pMFa (Kurjan and Herskowitz, Cell 30:933-943 (1982)), pJRY88 (Schultz et al., Gene 54:113-123 (1987)), and pYES2 (Invitrogen Corporation, San Diego, Calif.). Protocols for the transformation of yeast and fungi are well known to those of ordinary skill in the art (see Hinnen et al., Proc. Natl. Acad. Sci. USA 75:1929 (1978); Itoh et al., J. Bacteriology 153:163 (1983), and Cullen et al. (BiolTechnology 5:369 (1987)).

Mammalian cells suitable for carrying out the present invention include, among others: COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573) and NS-1 cells. Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 (Seed, B., Nature 329:840 (1987)) and pMT2PC (Kaufman et al., EMBO J. 6:187-195 (1987)).

Given the teachings provided herein, promoters, terminators, and methods for introducing expression vectors of an appropriate type into plant, avian, and insect cells may also be readily accomplished. For example, within one embodiment, the proteins of the invention may be expressed from plant cells (see Sinkar et al., J. Biosci (Bangalore) 11:47-58 (1987), which reviews the use of *Agrobacterium rhizogenes* vectors; see also Zambryski et al., Genetic Engineering, Principles and Methods, Hollaender and Setlow (eds.), Vol. VI, pp. 253-278, Plenum Press, New York (1984), which describes the use of expression vectors for plant cells, including, among others, PAPS2022, PAPS2023, and PAPS2034)

Insect cells suitable for carrying out the present invention include cells and cell lines from *Bombyx, Trichoplusia* or *Spodotera* species. Baculovirus vectors available for expression of proteins in cultured insect cells (SF 9 cells) include the pAc series (Smith et al., Mol. Cell. Biol. 3:2156-2165 (1983)) and the pVL series (Lucklow, V. A., and Summers, M. D., Virology 170:31-39 (1989)). Some baculovirus-insect cell expression systems suitable for expression of the recombinant proteins of the invention are described in PCT/US/02442.

Alternatively, the heavy and light chains of the antibody may also be expressed in non-human transgenic animals such as rats, rabbits, sheep and pigs (Hammer et al. Nature 315:680-683 (1985); Palmiter et al. Science 222:809-814 (1983); Brinster et al. Proc. Natl. Acad. Sci. USA 82:4438-4442 (1985); Palmiter and Brinster Cell 41:343-345 (1985) and U.S. Pat. No. 4,736,866).

One inefficiency in generating a library of monoclonal antibodies that has members that target all the components of a mixture of antigenic substances arises because the majority of the monoclonal antibodies may target a minority of the components, often the most abundant or immunogenic of the components. The invention provides a method for avoiding redundancy and the repeated cloning of genes that encode antibodies that target antigens that are the same as those targeted by monoclonal antibodies that have already been generated. It enables clones of for example rabbit ASC to be screened to determine whether or not the antibody they produce is binding to a novel target not recognized by monoclonal antibodies that have already been cloned. The method requires that, as segments of DNA encoding the antigen-binding regions of different rabbit monoclonal antibodies are obtained, they are expressed as part of chimeric molecules such as antibodies with human constant regions. This enables one to readily distinguish the binding of new rabbit monoclonal antibodies to the target cells from binding of these chimeric antibodies already shown to bind to antigens on the target cell. Thus before use in screening for rabbit monoclonal antibodies specific for new antigens for example on a cell surface, target cells are exposed to pools of existing rabbit-human chimeric monoclonal antibodies so that the chimeric antibodies mask their target antigens and prevent binding of any new rabbit antibody specific for the same antigen. Because the detection system utilizes an immuno-fluorescent reagent specific for the constant region of rabbit antibodies it will not recognize the human constant regions on these chimeric antibodies that are masking their targets on the cell. Only if the target of a rabbit antibody made by a new clone of ASC is novel in terms of the growing panel of antibodies, will its binding to the target cell be detected. The same principles apply to isolation of monoclonal antibodies to different parts of the one substance (e.g. epitopes on a protein). Thus, the invention includes a method of minimizing redundancy in a library of antibodies to a desired antigen or mixture of desired antigens comprising the steps:

a) providing an antibody-secreting cell according to the methods of the invention;

b) cloning nucleic acid molecules that encode the variable regions of the heavy and light chains of the antibody made by the antibody-secreting cell;

c) generating a chimeric molecule comprising the antigen-binding regions of the heavy and light chains of the antibody made by the antibody-secreting cell and domains other than the immunoglobulin constant regions of the species from which the antibody-secreting cell is derived;

d) providing another antibody-secreting cell according to any of the methods of the invention;

e) making a mixture comprising said chimeric molecule from step (c) with the desired antigen or mixture of antigens;

f) adding to the mixture of step (e) the antibodies secreted by the antibody-secreting cell of step (d);

g) adding to the mixture of step (f) a detectable reagent that binds specifically to the constant region of the species from which the antibody-secreting cell of step (d) was derived from; and h) determining whether the antibodies made by the antibody-secreting cell from step (d) are binding to an antigen or antigenic determinant distinct from that bound by the chimeric molecule by detecting the detectable label.

In one embodiment, the domain of step (c) comprises the constant region from a different species from which the antibody-secreting cell was derived from.

In another embodiment, steps (a) to (c) are repeated more than once so that there is more than one chimeric molecule from different antibody secreting cells and the mixture of step (e) comprises more than one chimeric molecule.

The above disclosure generally describes the present invention. A more complete understanding can be obtained by reference to the following specific examples. These examples are described solely for the purpose of illustration and are not intended to limit the scope of the invention. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present invention:

EXAMPLES

1. Isolation of Rabbit ABC from a Recently Immunized Rabbit and Expansion to Clones of Antibody-Secreting Cells Blood (20 ml) from a rabbit immunized with a fusion protein of GST and the human protein M-Ras and last boosted 6 days previously was collected into heparin and PBMC prepared. The antigen was biotinylated using standard methods specified by the manufacturer. Aiming for an average of 2 biotin molecules per antigen molecule. PIERCE product 'EZ-link Sulfo-NHS-SS-Biotin' (Cat #21331) was allowed to come to room temperature before the reagent is opened (stored at −80° C. between uses). A 20 mg/mL dilution was prepared in dH$_2$O. Using calculations based on the molecular weights of the targeted antigen and the biotinylation reagent (606.7 g/mol), an 8 to 20-fold molar excess of biotin was used in the reaction. The two components were combined in PBS, and left to stand at RT for 30 min. The mixture was added to dialysis tubing, and the excess free biotin is removed by dialysis in PBS overnight. The buffer was changed twice prior to harvesting the biotinylated product. Aliquots of biotinylated product were stored at −80° C. The ratio of the fluorochrome-conjugated streptavidin or avidin to antigen should be equal to a 1:1 ratio of biotin-binding sites to antigen. The ration of the two complexes were chosen so they bound equally to cells with specific receptors. (The ratios of each that are needed can be estimated and checked by using flow cytometry to titrate their ability to bind to beads coupled with an IgG fraction of serum from the immunized donor from which AFC will be obtained). To double label rabbit cells that were binding specifically to the antigen, 5 ug of DyLight-conjugated steptavidin (Pierce Biotechnology) was combined with 5 ug of biotinylated-GST-M-Ras in one tube, and 5 ug of fluorescein-conjugated avidin (Pierce Biotechnology) was added to 5 ug of biotinylated-GST-M-Ras in another tube.

After incubation at 37° C. for 30 min in the dark, the reagents were mixed with the rabbit PBMCs in a volume of 100 uL of 1% BSA in PBS. A FACS Vantage with DIVA optical bench was use to sort single cells that were positive for both dyes and that bound the two dyes proportionately (ie lay on a diagonal on a plot of the fluorescence intensities at the optimal emission wave-lengths of Dylight and fuoroscein). The sorted cells were cultured for 7 days as described below and 80% generated clones that secreted antibodies specific for GST-M-Ras.

2. Culture of Rabbit AFC for Clonal Expansion and Differentiation and Testing of Specificity of Secreted Antibodies The method is based on that of Zubler and colleagues (Wen et al., 1987) modified by the use of a supernatant of cultures of activated rabbit instead of human T cells. To prepare supernatant of cultures of activated T cells, blood, ideally from multiple rabbits is collected into heparin is diluted with an equal volume of sterile PBS and PBMC are fractionated using Ficoll. PBMC are diluted to $0.5 \times 10^6$ cells per mL in complete RPMI-1640 and stimulated with Concanavalin A (10 ug/mL final) and PMA (20 ng/mL final). Supernatant is harvested on days 2, 4 and 6 and is replaced with fresh RPMI The supernatant is freed of any cells by centrifugation, pooled and stored at 4 C.

To remove any IgG that would complicate the monitoring of secretion of immunoglobulins in cultures to which it is added, the supernatant is depleted of IgG by adsorption on a mixture of washed Protein A-coupled and Protein-G coupled beads (Amersham). Each batch of supernatant is tested to determine the optimal concentration for promoting the growth of clones of rabbit ASC.

To expand single rabbit AFC into clones of ASC, single cells are sorted by FACS in to the wells of a 96-well microculture plate, each of which contains RPMI with 10% serum and 0.5 mM 2-mercaptoethanol. Confirmation that wells contain a single cell is obtained by fluorescent microscopic visualization of the Hoescht 33342 staining of the cell in each well. To each well is added 20,000 irradiated EL4 B5 cells (5000 Rads), 33,000 heat-inactivated staphylococci ("Pansorbin cells"), and a preoptimized dilution of T lymphocyte supernatant, the total volume being 200 uL. The 96-well culture plates are left in the tissue culture incubator for ~7 days.

The culture supernatant is harvested into equal volumes of 1% BSA in PBS and kept at 4° C. for analysis by ELISA. Aliquots of harvested culture supernatant are transferred to ELISA plates coated with the target antigen and in parallel to ELISA plates coated with goat anti-rabbit IgG to detect levels of total IgG. Uncoated wells are included as a negative control.

The single ASC from Example 1 that were sorted into 96-well plates were cultured as described for 7 days. Supernatants were harvested and tested by ELISA for reactivity with the antigen GST-M-Ras or for production of IgG. It was observed that 80% of the cultures made IgG antibodies specific for the antigen GST-M-Ras.

3. Recovery of Genetic Information Encoding the Antigen-Binding Site of a Desired Antibody from Clones of Rabbit Antibody-Secreting Cells Single rabbit ABC's from a rabbit immunized 240 days previously with human Fab fragments of a human immunoglobulin MJ5 were sorted into 96-well plates by the FACS Vantage using as a criterion proportionate binding to both preformed complexes of biotinylated Fab MJ5 with phycoerythrin-streptavidin and biotinylated Fab MJ5 with fluoroscein conjugated Avidin. Cells were cultured for 9 days as in the Example above and supernatants were harvested an tested in ELISA assays for the presence of antibodies with the desired specificity for the Fab fragment of MJ5. Wells D10 and E5 were identified as containing useful antibodies. To recover the genetic information encoding their antigen-binding sites RT-PCR was performed. To prepare RNA an "Absolutely RNA Microprep Kit" (Cat #400805 Stratagene) was used. All work is performed in a laminar flow cabinet using filtered pipetman tips and new gloves. The cells are carefully removed from the correct wells identified by screening for binding to antigen and resuspended gently with a pipetman and transferred to a 1.5 mL eppendorf tube. The well is rinsed with ~200 ul sterile PBS and this is added to the same eppendorf tube. The cells are spun at 5000 rpm for 3 min at 4° C. and the supernatant is transferred to a new, labeled eppendorf tube.

50-100 ul of Lysis buffer with fresh mercaptoethanol from the Stratagene kit is added to the cell pellet which is Vortexed "hard and short". An equal volume of 70% ethanol is added to the cell lysate and Vortexed. at high speed for 5 seconds. The mixture is transferred to a RNA-Binding spin cup seated in a 2 ml collection tube and is spun at 60 s, 14,000 rpm at 4° C. The filtrate is discarded and the spin cup retained in collection tube. 600 uL of 1× Low Salt Wash Buffer (prepared with fresh 100% ethanol) and the cup spun at max speed for 1 min. The filtrate is discarded and the spin cup spun for 2 min. at max. speed to dry to fiber matrix. 5 ul of Rnase-free Dnase1 is mixed with the supplied Dnase Digestion Buffer (25 ul) and is added directly to the spin cup. Cap The tube is capped and incubated at 37 C for 20 min. 500 ul of 1× High Salt Wash Buffer (again, prepared from higher X stock using fresh 100% ethanol) is added and the tube capped and spun at maximum speed for 1 min. The filtrate is discarded and to the spin cup is added 600 uL 1× Low Salt Wash Buffer. The tube is capped and spin at max. speed for 60 sec. (4 C). The procedure is repeated with 300 ul 1× Low Salt Wash Buffer. After a final spin at max speed for 2 minutes to dry the fiber matrix, the spin cup is transferred to a new 1.5 mL collection tube. 30 ul of pre-warmed (60 C) Elution Buffer is added directly onto the fiber matrix and the tube is capped and incubated at room temperature for 2 minutes and spun at maximum speed for 1 min and the collection tube with RNA set aside on ice. The elution step is then repeated with the RNA eluate placed into a second tube.

The following primers are used for amplification of the variable regions of the rabbit kappa chain and the heavy chain:

VK1S
(SEQ ID NO: 1)
GCA GCT AGC CACC ATG GAC ACG AGG GCC CCC ACT CAGC

CK1AS
(SEQ ID NO: 2)
TGG TGG GAA GAT GAG GAC AGT AGG

J1K1
(SEQ ID NO: 3)
ATA GCG GCC GC AGT TTT GAT TTC TAC CTT GGT GCC A

J2K1
(SEQ ID NO: 4)
ATA GCG GCC GC AGT TTT GAC CAC CAC CTC GGT CCC

J3K1
(SEQ ID NO: 5)
ATA GCG GCC GC AGT TTT GAT TTC CAG TTT GGT CCC

J4K1
(SEQ ID NO: 6)
ATA GCG GCC GC AGT TTT GAT CTC CAC CAT GGT CCC

J5K1
(SEQ ID NO: 7)
ATA GCG GCC GC AGT TTT GAT CTC CAG CTT GGT CTC (The above 5 JK primers are combined to create the "Jk mix".)

VH1S
(SEQ ID NO: 8)
TCG GCT AGC CACC ATG GAG ACT GGG CTG CGC TGG CTT

CH1AS
(SEQ ID NO: 9)
GGC CAG TGG GAA GAC TGA CGG AGC CTT A

J1H
(SEQ ID NO: 10)
ATA AAG CTT GC TGA AGA GAT GGT GAC CAG GGT

J2, 3, 4H
(SEQ ID NO: 11)
ATA AAG CTT GC TGA GGA GAC GGT GAC CAG GGT

J5, 6H
(SEQ ID NO: 12)
ATA AAG CTT GC TGA AGA GAC GGT GAC GAG GGT (The above three J-H primers are combined in equal portions to create "JH mix".)

cDNA Synthesis From 100 pmol/uL stocks of the 'CK1AS' and 'CH1AS' primers (above) 'working' stocks of 20 pmol/ul are made with DEPC-treated water. To each PCR tube, the following reagents are added: 1 uL dNTPs (10 mM) and either 0.5 uL 'CK1AS' OR 0.5 uL 'CH1AS' primers (from the 20 pmol/uL 'working stocks'). From RNA samples kept on ice, 8 uL is added to each tube. The mix is placed immediately back on ice. In PCR machine, with a lid temp=70° C., the above mixture is incubated at 65° C. for 5 min. The tubes are then spun briefly at maximal speed in cold microcentrifuge. The equivalent of: 4 ul 5× First Strand Buffer, 2 uL 0.1 M DTT and 1 uL Rnase Inhibitor is added to each sample. The three components can be 'pre-mixed' at the time of the experiment and added as a "master mix" to each tube of RNA. All enzymes are kept on ice or in cold block to maintain their integrity. The new mixtures of RNA+Rnase Inhibitor are taken back to the PCR machine on ice. The middle step of the program continues as follows: 2 min at 42° C., PAUSE, then 1 uL of Superscript II Rnase H-RT is added directly to the 'PCR' tubes. Gloves are changed in between handling each of the samples. The final stages of the RT are: 42° C. for 60 min., 70° C. for 15 min., then the tubes are held at 4° C.

PCR: For amplification of the kappa and heavy variable regions, PCR reactions are set-up in a laminar flow hood, where gloves are changed often, only filtered tips are used for the pipetmen, and tips are ejected outside of the hood to prevent cross-contamination between samples.

"Master Mixes" for the 'Kappa' and 'Heavy' Chains were prepared as follows:

| Reagent | 15X Master Mix (uL) | 1X Master Mix (uL) (for Reference) |
|---|---|---|
| DEPC-water (Invitrogen) | 577.5 | 38.5 |
| 10 × Pfx Buffer (Invitrogen) | 75.0 | 5.0 |
| 10 mM dNTPs (Invitrogen) | 22.5 | 1.5 |
| 50 mM MgSO4 (Invitrogen) | 15.0 | 1.0 |
| "VK1S" OR "VH1S" (20 pmol/uL) | 11.25 | 0.75 |
| "Jkmix" OR "JHmix" (20 pmol/uL) | 11.25 | 0.75 |
| Platinum Pfx (Invitrogen) | 7.5 | 0.5 |
| | 720 | 48.0 |

Following preparation of the "Master Mixes" above and following aliquoting them to new PCR tubes, 2 uL of the appropriate "RT-product", or cDNA, kept on ice, is added to each sample. The appropriate positive and negative controls are included. PCR tubes are taken to the PCR machine on ice. With a lid temp=94 C, the PCR program is proceeds as follows: 1) 94° C. for 3 min.; 2) 94 C for 1 min.; 3) 60° C. for 1 min.; 4) 68° C. for 1 min; Repeat 2-4, 39×, then final extension, 5) 68° C. for 7 min. Hold at 4° C. Analysis of PCR products is performed on a 1.0% agarose gel with a 1/10,000 dilution of 'SyBr Safe' (Invitrogen). The 100 bp DNA ladder is used as a marker. The addition of ~5-7 uL of PCR product+ 1-2 uL loading dye is added to each well of the agarose gel. The gel was run for ~1 hr at ~90 V. Bands for kappa and heavy chains were visible running between 400 and 500 bp (FIG. 1). These were cut out and cloned into the TOPO vector and sequenced. The sequences of the heavy and kappa chain regions of clones E10 and D5 are shown (FIG. 2).

4. Expression of Variable Region Genes as the Binding Sites of IgG Monoclonal Antibodies The PCR products corresponding to the variable regions of the heavy and light chains were inserted in frame with the constant regions into the respective pLC and pHC vectors. These vectors which respectively encode the constant regions of the human kappa and gamma 1 heavy chains.

Figure 3:
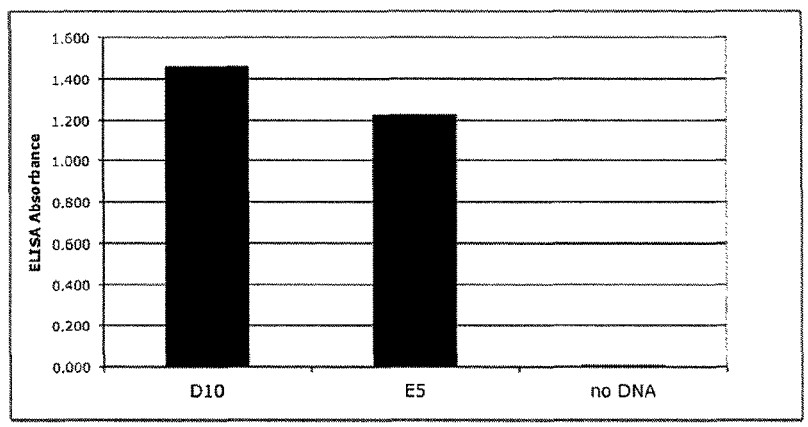
FIG. 3 shows the optical density (mean of 3 replicates) of ELISA assays in plates coated with the human Fab fragment MJ5, of supernatants of cultures of BOSC cells transfected with the heavy and light chain genes encoding IgG1 antibodies in which the variable regions of the heavy and light chain genes were copied respectively from the D10 clone of rabbit ASC (D10) and the E5 clone (E5). Also shown is a supernatant from a culture of untransfected BOSC cells demonstrating that it has no ability to bind to the human Fab fragment.

BOSC cells were split using trypsin-EDTA (Invitrogen, Cat. #25200-073) into a 6-well culture dish in preparation for transfection. DNA that corresponds to the pLC and pHC vectors modified by insertion of the appropriate variable region genes was mixed, according to the Invitrogen instructions, with 'Lipfectamine' (Invitrogen, Cat. #18324-012) and 'Optimem' (Invitrogen, Cat. #31985-070). The BOSC cells were 70-80% confluent and growing in complete DMEM. Immediately prior to the addition of the DNA mixture, the DMEM supernatant was aspirated from the tissue culture dish of BOSC's (one well at a time). The Lipofectamine+DNA+ Optimem mixture was added dropwise to the cells by pipetman. Then 2 mL of further Optimem was added to the well. Positive and negative controls were included. The next day, the media in the wells was supplemented with 2 mL of complete DMEM. Supernatant is harvested and fresh DMEM is added daily. Harvested supernatant was spun at 1500 rpm for 5-10 min to pellet any cells and stored at 4° C. with 0.01% Na azide (final). Shown are ELISA assays demonstrating that the supernatant of cultures of BOSC cells transfected with the heavy and light chain constructs containing the variable region genes of the antibodies copied from the clones in wells E10 and D5 both bound strongly to MJ5 Fab fragments (FIG. 3).

5. Obtaining a Population of Cells Naturally Enriched in Antibody-Secreting Cells that at a Usefully High Frequency are Likely to be Producing a Human Antibody Specific for Components of the Influenza Virus A human is re-immunized ("boosted") with a standard dose of influenza vaccine such as INFLUVAC (Solvay Pharma, Ontario) and a 50 ml sample of blood is taken 6 days later into a solution containing an anticoagulant such as heparin, all procedures being carried out under aseptic conditions with sterile reagents. The anticoagulated blood is transferred into 50 ml centrifuge tubes, and a buffy coat is obtained by centrifugation: at 1700 rpm for 25 mins (with no brake). Peripheral blood mononuclear cells (PBMC) are enriched using Ficoll-Hypaque. The buffy coat is diluted with phosphate-buffered saline and 30 ml are slowly overlayed over 10 ml of Ficoll in a 50 ml conical tube. The tubes are spun in a bench centrifuge at 2000 rpm for 20 min, at RT, with no brake.

The layer of mononuclear cells between the Ficoll and the plasma is collected into fresh tubes (combine 2 Ficoll layers into 1 tube) and Hanks' buffered salt solution (HBBS) is added to top up the tube which is spun at 1500 rpm for 10 min.

After pouring off the supernatant, the tube is flicked to loosen pellet and two pellets are pooled into a tube with 50 ml HBBS and centrifuged at 800 rpm for 10 min. After repeating the wash the cells are suspended in HBBS.

6. Isolation of ASC from a Population of Cells Naturally Enriched in Antibody-Secreting Cells that at a Usefully High Frequency are Likely to be Producing a Human Antibody Specific for Components of the Influenza Virus Using Cell-Surface Markers Peripheral blood mononuclear cells (PBMC) naturally enriched in antibody-secreting cells that at a usefully high frequency are likely to be producing a human antibody specific for components of the influenza virus from Example 5 are suspended in PBS. To this tube are added pre-optimized amounts of monoclonal antibodies labelled with fluorochromes suited for combined use in flow cytometry and specific for CD19, CD27, CD38, IgG and HLA-DR. After mixing on ice for 30 minutes, the cells are washed free of unbound antibody by centrifugation and re-suspended in PBS buffer and subjected to flow cytometry on a FACS Vantage with a DIVA optical bench. Cells expressing IgG, low levels of CD19 and high levels of CD38, CD27 and HLA-DR are sorted for analysis or into single wells for analysis of the specificity of the antibody they produce or for direct RT-PCR to clone the genes encoding the variable regions of the antibody they produce.

7. Isolation of ASC from a Population of Cells Naturally Enriched in Antibody-Secreting Cells that at a Usefully High Frequency are Likely to be Producing a Human Antibody Specific for Components of the Influenza Virus Using a Reverse Hemolytic Plaque Assay The PBMC enriched in ASC making antibodies specific for components of influenza virus from a procedure such as Example 6 are added in a series of dilutions in buffered tissue culture medium, (HEPES-buffered RPMI-1640 with 10% fetal calf serum and 0.5 mM 2-mercaptoethanol) to a mixture of protein-A coated sheep erythrocytes (final concentration 1%), a source of complement and antibodies specific for human IgG in a modification of "reverse" hemolytic plaque assay (Gronowicz et al., 1976). In the present invention the Reverse Hemolytic Plaque Assay is modified by performing it in a monolayer under a layer of mineral oil. This is based on a monolayer version of the antigen-specific hemolytic plaque assay described by Cunningham and Szenberg (Cunningham & Szenberg, 1968) as modified by Nossal to enable the facile isolation of individual ASC that produce plaques (Nossal et al., 1968). Coupling of SRC with Protein A is conveniently achieved using chromic chloride by methods well-described in the literature (Goding, 1976) that briefly involve washing SRC with normal saline, 125 uL of packed cells in 2 mL of saline with 25 uG of protein A and while mixing adding of 0.3% of chromic choride. After holding at room temperature for 10 minutes, the reaction is stopped with phosphate-buffered saline and the SRC washed 4 times. As a source of complement, a final concentration of ~5% guinea-pig serum is included. Before use the guinea-pig serum is sequentially pre-absorbed by agitating it for 60 minutes at 4° C. with packed SRC and then with protein A-coated Sepharose beads. The mixture also contains a pre-optimized dilution of rabbit anti-human IgG antibodies that will bind to and form complexes with the antibodies secreted by the ASC.

Drops of the mixture of 1-10 microliters are placed with a pipette on a microscope slide under a thin layer of mineral oil. The slide is incubated at 37° C. for about 30 minutes by which time plaques of lysed SRC should be evident under a microscope. At the correct dilution of the PBMC population, plaques should contain a single large central cell that is secreting the antibodies responsible for the plaque. The central cell is transferred by micromanipulation for recovery of the genetic information encoding the antigen-binding site of a desired antibody.

8. RT-PCR on Fixed Cells

To enable the use of FACS to identify and isolate ASC using antibodies to intracellular antibodies or using antigens to identify ASC that make antibodies specific for that antigen, it is necessary to fix cells and permeabilize them. For this purpose cells are washed with PBS and fixed with 1% formaldehyde in PBS for 10 minutes at room temperature and washed with PBS. For staining with antibodies, the fixed cells are held on ice for 30 minutes with a mixture containing labeled antibodies specific for IgG antibodies of the species of the ASC, saponin (2%) to permeabilize the cells and RNAse inhibitors in PBS with 1% BSA. After washing thoroughly in PBS with 1% BSA, the formaldehyde-induced cross-linking in the fixed cells is reversed by heating at 70° C.

for 30 minutes. The cells are placed on ice and 3 uL of 5% NP40 is added to the tube. The RT PCR then proceeds as usual.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

FULL CITATIONS FOR REFERENCES REFERRED TO IN THE SPECIFICATION

Acton, S., Resnick, D., Freeman, M., Ekkel, Y., Ashkenas, J. & Krieger, M. (1993). *J Biol Chem*, 268, 3530-7.
Andersson, J., Sjoberg, O. & Moller, G. (1972). *Eur J Immunol*, 2, 349-53.
Asakura, E., Tojo, N. & Tanabe, T. (1999). *Cell Prolif*, 32, 185-94.
Babcook, J. S., Leslie, K. B., Olsen, O. A., Salmon, R. A. & Schrader, J. W. (1996). *Proceedings of the National Academy of Sciences of the United States of America*, 93, 7843-8.
Barington, T., Heilmann, C. & Andersen, V. (1990a). *Scand J Immunol*, 31, 515-22.
Barington, T., Heilmann, C. & Andersen, V. (1990b). *Scand J Immunol*, 31, 515-22.
Bernasconi, N. L., Traggiai, E. & Lanzavecchia, A. (2002). *Science*, 298, 2199-202.
Carroll, S. & Al-Rubeai, M. (2005). *J Immunol Methods*, 296, 171-8.
Cassese, G., Arce, S., Hauser, A. E., Lehnert, K., Moewes, B., Mostarac, M., Muehlinghaus, G., Szyska, M., Radbruch, A. & Manz, R. A. (2003). *J Immunol*, 171, 1684-90.
Coronella, J. A., Telleman, P., Truong, T. D., Ylera, F. & Junghans, R. P. (2000). *Nucleic Acids Res*, 28, E85.
Cunningham, A. J. & Szenberg, A. (1968). *Immunology*, 14, 599-600.
Diamantstein, T., Blitstein-Willinger, E. & Schulz, G. (1974). *Nature*, 250, 596-7.
Ettinger, R., Sims, G. P., Fairhurst, A. M., Robbins, R., da Silva, Y. S., Spolski, R., Leonard, W. J. & Lipsky, P. E. (2005). *J Immunol*, 175, 7867-79.
Goding, J. W. (1976). *J Immunol Methods*, 10, 61-6.
Greaves, M., Janossy, G. & Doenhoff, M. (1974). *J Exp Med*, 140, 1-18.
Grewal, T., de Diego, I., Kirchhoff, M. F., Tebar, F., Heeren, J., Rinninger, F. & Enrich, C. (2003). *J Biol Chem*, 278, 16478-81.
Gronowicz, E., Coutinho, A. & Melchers, F. (1976). *Eur J Immunol*, 6, 588-90.
Heilmann, C., Henrichsen, J. & Pedersen, F. K. (1987). *Scand J Immunol*, 25, 61-7.
Heilmann, C. & Pedersen, F. K. (1986). *Scand J Immunol*, 23, 189-94.
Horst, A., Hunzelmann, N., Arce, S., Herber, M., Manz, R. A., Radbruch, A., Nischt, R., Schmitz, J. & Assenmacher, M. (2002). *Clin Exp Immunol*, 130, 370-8.
Kawai, T. & Akira, S. (2005). *Curr Opin Immunol*, 17, 338-44.

Kincade, P. W., Ralph, P. & Moore, M. A. (1976). *J Exp Med*, 143, 1265-70.
Kindler, V., Matthes, T., Jeannin, P. & Zubler, R. H. (1995). *Eur J Immunol*, 25, 1239-43.
Kuppers, R., Zhao, M., Hansmann, M. L. & Rajewsky, K. (1993). *Embo J*, 12, 4955-67.
Lagerkvist, A. C., Furebring, C. & Borrebaeck, C. A. (1995). *Biotechniques*, 18, 862-9.
Lange, M., Le Guern, C. & Cazenave, P. A. (1983). *J Immunol Methods*, 63, 123-31.
Manz, R., Assenmacher, M., Pfluger, E., Miltenyi, S. & Radbruch, A. (1995). *Proc Natl Acad Sci USA*, 92, 1921-5.
Manz, R. A., Thiel, A. & Radbruch, A. (1997). *Nature*, 388, 133-4.
Nossal, G. J., Cunningham, A., Mitchell, G. F. & Miller, J. F. (1968). *J Exp Med*, 128, 839-53.
Nossal, G. J. & Schrader, J. W. (1975). *Transplantation Reviews*, 23, 138-58.
Odendahl, M., Mei, H., Hoyer, B. F., Jacobi, A. M., Hansen, A., Muehlinghaus, G., Berek, C., Hiepe, F., Manz, R., Radbruch, A. & Dorner, T. (2004). *Blood*.
Odendahl, M., Mei, H., Hoyer, B. F., Jacobi, A. M., Hansen, A., Muehlinghaus, G., Berek, C., Hiepe, F., Manz, R., Radbruch, A. & Dorner, T. (2005). *Blood*, 105, 1614-21.
Ozaki, K., Spolski, R., Ettinger, R., Kim, H. P., Wang, G., Qi, C. F., Hwu, P., Shaffer, D. J., Akilesh, S., Roopenian, D. C., Morse, N. C., 3rd, Lipsky, P. E. & Leonard, W. J. (2004). *J Immunol*, 173, 5361-71.
Pasqualini, R. & Arap, W. (2004). *Proc Natl Acad Sci USA*, 101, 257-9.
Ruhl, H., Vogt, W., Bochert, G. & Diamantstein, T. (1974). *Immunology*, 26, 937-41.
Sanderson, R. D., Lalor, P. & Bernfield, M. (1989). *Cell Regul*, 1, 27-35.
Schrader, J. W. (1973a). *Journal of Experimental Medicine*, 138, 1466-80.
Schrader, J. W. (1973b). *Journal of Experimental Medicine*, 137, 844-9.
Schrader, J. W. & Nossal, G. J. (1974). *Journal of Experimental Medicine*, 139, 1582-98.
Steenbakkers, P. G., van Wezenbeek, P. M. & Olijve, W. (1993). *J Immunol Methods*, 163, 33-40.
Tangye, S. G., Avery, D. T. & Hodgkin, P. D. (2003). *J Immunol*, 170, 261-9.
Thomson, P. D. & Harris, N. S. (1977). *J Immunol*, 118, 1480-2.
Townsend, S. E., Goodnow, C. C. & Cornall, R. J. (2001). *J Immunol Methods*, 249, 137-46.
Vasilescu, J., Guo, X. & Kast, J. (2004). *Proteomics*, 4, 3845-54.
Vernino, L., McAnally, L. M., Ramberg, J. & Lipsky, P. E. (1992). *J Immunol*, 148, 404-10.
Viglianti, G. A., Lau, C. M., Hanley, T. M., Miko, B. A., Shlomchik, M. J. & Marshak-Rothstein, A. (2003). *Immunity*, 19, 837-47.
Vollmer, J., Tluk, S., Schmitz, C., Hamm, S., Jurk, M., Forsbach, A., Akira, S., Kelly, K. M., Reeves, W. H., Bauer, S. & Krieg, A. M. (2005). *J Exp Med*, 202, 1575-85.
Wang, X. & Stollar, B. D. (2000). *J Immunol Methods*, 244, 217-25.
Weitkamp, J. H., Kallewaard, N., Kusuhara, K., Feigelstock, D., Feng, N., Greenberg, H. B. & Crowe, J. E., Jr. (2003). *J Immunol Methods*, 275, 223-37.
Wen, L., Hanvanich, M., Werner-Favre, C., Brouwers, N., Perrin, L. H. & Zubler, R. H. (1987). *Eur J Immunol*, 17, 887-92.

I claim:
1. A method of generating monoclonal antibodies specific for a desired antigen, comprising the steps:
   a) providing a sample from an animal that was exposed to the desired antigen 4-8 days prior, wherein the sample comprises a population of antibody-secreting cells that are secreting antibodies specific for the desired antigen;
   b) increasing a concentration of antibody-secreting cells in the sample by enriching for cells with general features characteristic of antibody-secreting cells;
   c) isolating a single antibody-secreting cell;
   d) cloning a first nucleic acid molecule that encodes the variable region of the heavy chain of the antibody made by the single antibody-secreting cell, and cloning a second nucleic acid molecule that encodes the variable region of the light chain of the antibody made by the single antibody-secreting cell; and
   e) transforming host cells with the cloned first and second nucleic acid molecules and expressing the first and second nucleic acid molecules that encode the variable regions or parts thereof of the heavy and light chains of the antibody made by the antibody-secreting cell;
   wherein steps d) and e) avoid the mixing of the first and second nucleic acid molecules with other nucleic acid molecules encoding heavy and/or light chain variable regions from different antibodies; and
   wherein the concentration of antibody-secreting cells in the sample by enriching for cells with general features characteristic of antibody-secreting cells according to b) is increased without using the desired antigen by a method selected from:
      i) a method comprising enriching for cells or depleting cells in the sample with surface markers;
      ii) a method comprising increasing the concentration of cells in the sample for cells with enlarged endoplasmic reticulum and/or Golgi apparatus as compared with other cells in the sample;
      iii) a method comprising increasing the concentration of cells in the sample that have high levels of intracellular immunoglobulin as compared with other cells in the sample; and
      iv) a method comprising any combination of i), and/or iii).

2. The method according to claim 1, wherein the animal is human and wherein the concentration of antibody-secreting cells in the sample by enriching for cells with general features characteristic of antibody-secreting cells according to b) is increased by enriching for cells expressing low levels of CD19 and high levels of CD27 and CD38.

3. The method according to claim 2, further comprising enriching for cells expressing high levels of HLA-DR.

4. The method according to claim 1, wherein the concentration of antibody-secreting cells in the sample by enriching for cells with general features characteristic of antibody-secreting cells according to b) is increased by increasing the concentration in the sample for cells with enlarged endoplasmic reticulum or Golgi apparatus by selectively staining the endoplasmic reticulum or Golgi apparatus with fluorescent dyes that stain the endoplasmic reticulum or Golgi apparatus in viable cells and isolating in c) the single antibody-secreting cell with a fluorescence-activated cell sorter.

5. A method of generating monoclonal antibodies specific for a desired antigen, comprising the steps:
   a) providing a sample from an animal that was exposed to the desired antigen 4-8 days prior, wherein the sample comprises a population of antibody-secreting cells that are secreting antibodies specific for the desired antigen;
   b) allowing cells in the sample to adhere to particles that are coated with an agent that captures antibodies secreted by an individual antibody-secreting cell and identifying antibody-secreting cells by detecting the captured antibodies with detectable reagents;
   c) isolating a single antibody-secreting cell;
   d) cloning a first nucleic acid molecule that encodes the variable region of the heavy chain of the antibody made by the single antibody-secreting cell, and cloning a second nucleic acid molecule that encodes the variable region of the light chain of the antibody made by the single antibody-secreting cell; and
   e) transforming host cells with the cloned first and second nucleic acid molecules and expressing the first and second nucleic acid molecules that encode the variable regions or parts thereof of the heavy and light chains of the antibody made by the antibody-secreting cell;
   wherein steps d) and e) avoid the mixing of the first and second nucleic acid molecules with other nucleic acid molecules encoding heavy and/or light chain variable regions from different antibodies and wherein in (b) the enrichment is achieved without use of the desired antigen.

6. The method of claim 5, wherein the agent that captures antibodies secreted by the individual cells comprises Protein A, Protein G, or antibodies that bind to antibodies from the species of animal from which the sample was obtained.

7. A method of generating monoclonal antibodies specific for a desired antigen using a reverse plaque assay, comprising the steps:
   a) providing a sample from an animal that was exposed to the desired antigen 4-8 days prior, wherein the sample comprises a population of recently generated antibody-secreting cells that are secreting antibodies specific for the desired antigen;
   b) incubating the sample with erythrocytes coated with an agent that captures secreted antibodies in liquid or a semi-solid medium that includes, or to which is added, a source of complement and a secondary antibody that binds to and forms complexes with antibodies secreted by the antibody-secreting cells to form a mixture, wherein the agent that captures the antibodies is not the desired antigen;
   c) incubating the mixture to allow hemolytic plaques to develop;
   d) identifying individual hemolytic plaques;
   e) isolating the central single antibody-secreting cell that generated the individual hemolytic plaque;
   f) cloning a first nucleic acid molecule that encodes the variable region of the heavy chain of the antibody made by the single antibody-secreting cell, and cloning a second nucleic acid molecule that encodes the variable region of the light chain of the antibody made by the single antibody-secreting cell; and
   g) transforming host cells with the cloned first and second nucleic acid molecules and expressing the first and second nucleic acid molecules that encode the variable regions or parts thereof of the heavy and light chains of the antibody made by the antibody-secreting cell;
   wherein steps f) and q) avoid the mixing of the first and second nucleic acid molecules with other nucleic acid molecules encoding heavy and/or light chain variable regions from different antibodies.

8. The method of claim 7, wherein the agent that captures the secreted antibodies comprise Protein A, Protein G, or antibodies that bind to antibodies from the species of animal from which the sample was obtained.

9. The method according to claim 1; wherein isolating a single antibody secreting cell in (c) comprises first labeling the antibody-secreting cells with a label that enables single cells to be distinguished from multiple cells.

10. The method according to claim 9, wherein the label is Hoescht 33342, CFSE or PKH26.

11. The method according to claim 1, wherein (c) comprises isolating a single cell by limiting dilution.

12. The method according to claim 1, wherein (c) comprises isolating a single cell by micromanipulation.

13. The method according to claim 1, wherein the antibody-secreting cell is expanded to a clone prior to cloning the nucleic acid molecules.

14. The method according to claim 1, wherein the sample is a blood sample.

15. The method according to claim 1, wherein the concentration of antibody-secreting cells in the sample by enriching for cells with general features characteristic of antibody-secreting cells according to b) is increased by a method comprising enriching for cells that have high levels of CD138.

16. The method according to claim 2, further comprising depleting cells expressing high levels of CXCR3 and/or CXCR4 and/or CD20.

\* \* \* \* \*